(12) United States Patent
Chen et al.

(10) Patent No.: US 8,294,095 B2
(45) Date of Patent: Oct. 23, 2012

(54) APPARATUS OF PLURAL CHARGED PARTICLE BEAMS WITH MULTI-AXIS MAGNETIC LENS

(75) Inventors: Zhongwei Chen, San Jose, CA (US); Weiming Ren, San Jose, CA (US); Kenichi Kanai, Palo Alto, CA (US); Xuedong Liu, Cupertino, CA (US)

(73) Assignee: Hermes Microvision, Inc., Hsin-Chu (TW)

( * ) Notice: Subject to any disclaimer, the term of this patent is extended or adjusted under 35 U.S.C. 154(b) by 139 days.

(21) Appl. No.: 12/968,201

(22) Filed: Dec. 14, 2010

(65) Prior Publication Data

US 2012/0145900 A1 Jun. 14, 2012

(51) Int. Cl.
*H01J 29/56* (2006.01)
*G01N 23/225* (2006.01)
(52) U.S. Cl. .................................. 250/310; 250/396 ML
(58) Field of Classification Search .................. 250/310, 250/396 ML
See application file for complete search history.

(56) References Cited

U.S. PATENT DOCUMENTS

| 7,253,417 B2 * | 8/2007 | Frosien et al. ............. 250/396 R |
| 8,003,953 B2 * | 8/2011 | Chen et al. ............. 250/396 ML |
| 2008/0121810 A1 * | 5/2008 | Liu et al. ................. 250/396 ML |

* cited by examiner

*Primary Examiner* — Jack Berman
*Assistant Examiner* — Eliza Osenbaugh-Stewart
(74) *Attorney, Agent, or Firm* — Stout, Uxa, Buyan & Mullins, LLP

(57) ABSTRACT

An apparatus basically uses a simple and compact multi-axis magnetic lens to focus each of a plurality of charged particle beams on sample surface at the same time. In each sub-lens module of the multi-axis magnetic lens, two magnetic rings are respectively inserted into upper and lower holes with non-magnetic radial gap. Each gap size is small enough to keep a sufficient magnetic coupling and large enough to get a sufficient axial symmetry of magnetic scale potential distribution in the space near to its optical axis. This method eliminates the non-axisymmetric transverse field in each sub-lens and the round lens field difference among all sub-lenses at the same time; both exist inherently in a conventional multi-axis magnetic lens. In the apparatus, some additional magnetic shielding measures such as magnetic shielding tubes, plates and house are used to eliminate the non-axisymmetric transverse field on the charged particle path from each charged particle source to the entrance of each sub-lens and from the exit of each sub-lens to the sample surface.

23 Claims, 13 Drawing Sheets

US 8,294,095 B2

APPARATUS OF PLURAL CHARGED PARTICLE BEAMS WITH MULTI-AXIS MAGNETIC LENS

CROSS-REFERENCE TO RELATED APPLICATIONS

This application relates to co-pending U.S. application Ser. No. 12/636,007, filed Dec. 11, 2009 and entitled "A MULTI-AXIS MAGNETIC LENS." The foregoing application is commonly assigned and the entire contents are expressly incorporated herein by reference.

FIELD OF THE INVENTION

The present invention relates to a multi-axis magnetic immersion objective lens. More specifically, it relates to a multi-axis charged particle apparatus for obtaining a high spatial resolution and a high throughput in defect inspection of semiconductor wafer and mask.

BACKGROUND OF THE INVENTION

Defect inspection of semiconductor wafer and mask in IC manufacturing is an accepted significant production process for yield enhancement. The information obtained from a wafer defect inspection tool can be used to flag defective dies for repair, or improve wafer processing parameters. There are two main kinds of inspection tools used for defect inspection in semiconductor fabrication plants, i.e., optical inspection tool and electron beam inspection tool. The spatial resolution of an optical inspection tool is fundamentally limited by its larger wave diffraction spot because an optical wavelength is much longer than that of an electron beam. As critical dimensions of patterns on a wafer and a mask are required to become smaller and smaller, it is becoming incompetent. However, the throughput or called as inspection speed of an electron beam inspection tool is fundamentally limited by electron interaction or called as Coulomb Effect. As inspecting full wafer or full mask is becoming necessary, increasing its throughput is becoming a key issue. As a promising solution, using a plurality of electron beams to inspect wafer in parallel was provided many years ago.

The first patent using a multi-axis magnetic lens to separately focus several parallel electron beams was granted to Maekawa et al. in 1973 for throughput improvement of an IC pattern exposure system. The apparatus includes one common exciting coil 44, one york 43, and two magnetic conductor plates 41 and 42 with a plurality of through holes 1, 2 and 3 for the corresponding charged particle beam passing, which was proposed in U.S. Pat. No. 3,715,580 and is illustrated in FIG. 1A. Between a pair of aligned holes in the upper and lower magnetic conductor plates 41 and 42, a sub-lens such as 10 is formed, so as sub-lenses 20 and 30. The two magnetic conductor plates 41 and 42 are the pole pieces of these sub-lenses 10, 20 and 30. In this multi-axis magnetic lens, the magnetic fields of the sub-lenses are fundamentally different from each other in distribution pattern and strength as shown in FIG. 1B.

Comparing with a conventional single-axis magnetic lens, one main problem of this multi-axis magnetic lens is the magnetic field distribution of each sub-lens degenerates from axial symmetry to rotation symmetry and/or n-fold symmetry (FIG. 1B). As a result, besides an axisymmetric field or called as round lens field which focuses a particle beam, a lot of undesired non-axisymmetric transverse field components or called as high order harmonics in terms of Fourier analysis of magnetic field, such as dipole field and quadrupole field appear. The dipole field deflects the charged particle beams, makes the beam land on the imaging plane with an additional transverse shift, an additional tilt angle and additional aberrations. The quadrupole field adds astigmatism to the beam. To compensate the influence of each high order harmonic, at least one additional element generating the same type field is required to add to the electron optics system.

Another main problem of this multi-axis magnetic lens is the round lens field of the center sub-lens 20 is a little different from those of the peripheral sub-lenses 10 and 30. This problem results in that the charged particle beams 1, 2 and 3 respectively passing through the center sub-lens 20 and the peripheral sub-lenses 10 and 30 are not focused at the same imaging plane.

Many scientists who followed Maekawa's foot steps have tried many methods to solve these two main problems. For example, U.S. Pat. No. 6,750,455 of Lo et al. reduces the dipole field itself by using a plurality of dummy holes to improve the local structure symmetry of each sub-lens. U.S. Pat. No. 6,777,694 of Haraguchi compensates the dipole field influence by inserting a deflector group in each sub-lens hole. U.S. Pat. No. 6,703,624 of Haraguchi et al. nulls the round lens field difference among all the sub-lenses by changing the diameters of the two pole pieces or the gap size between the two pole pieces in each sub-lens to control the magnetic flux leakage. U.S. Pat. No. 6,703,624 of Haraguchi et al. and U.S. Pat. No. 7,253,417 of Frosien et al. compensate the round lens field difference by inserting an auxiliary round coil or an electrostatic lens in each sub-lens.

These previous methods were either making the magnetic conductor plate become larger, the multi-axis magnetic lens system bulky, or making it complicated. Chen et al. filed U.S. patent application Ser. No. 12/636,007 entitled "Multi-axis magnetic lens" in December 2009 to provide a better solution. Its main principle is shown in FIG. 2A by taking the sub-lens 30 in FIG. 1A as an example. In the sub-lens 30, two magnetic rings 32 and 33 are respectively inserted into the holes in the upper and lower magnetic plates 41 and 42, wherein 32 and 33 are respectively called as upper and lower pole-piece. A portion of the lower end of the upper pole-piece 32 extends inside a portion of the upper end of the lower pole-piece 33. Both of the upper pole-piece 32 and the lower pole-piece 33 are made of a magnetic material with a high permeability, and do not touch the inner sidewall of the correspondent hole. The spatial gap 34 and 35 is either a vacuum space or filled with a non-magnetic material. A space magnetic field along the optical axis 31 is generated through the space gap between the upper pole-piece 32 and the lower pole-piece 33. In FIG. 2A, the non-axisymmetric transverse field components almost become zero in the area inside the upper pole-piece 32 and the lower pole-piece 33, and are reduced by two magnetic tubes 36 and 37 to a level much lower than in FIG. 1A in the area outside the upper pole-piece 32 and the lower pole-piece 33. As an example the dipole field reduction is shown in FIG. 2B. The round lens field difference among all of the sub-lenses can be eliminated by appropriately choosing each non-magnetic gap (34 and 35) size. In this patent application, Chen et al. also provides an embodiment of multi-axis magnetic objective lens, as shown in FIG. 2C, wherein each sub-lens generates a magnetic field confined within the axial magnetic circuit gap between its upper and lower pole-pieces.

Nevertheless, it is well known that, compared with a radial-gap magnetic lens (having a radial magnetic circuit gap), this type of magnetic lens generates larger aberrations which damages spatial resolution, but requires small coil excitation (product of coil turns and coil current) which abates the issue of system overheat. In addition, a magnetic plate 50 with a plurality of through round holes is used to replace all of the individual magnetic tubes between the specimen 60 and the lower magnetic plate 42.

The present invention will adopt the main principle of Chen's multi-axis magnetic lens and further improve its performance as an immersion objective lens, so as to provide an apparatus which uses a plurality of charged particle beams to inspect a specimen in parallel with a high spatial resolution and a high throughput.

SUMMARY OF THE INVENTION

The object of this invention is to provide an apparatus employing a multi-axis magnetic lens and LVSEM (low-voltage scanning electron microscope) technology, which uses a plurality of low-energy charged particle beams to inspect a specimen in parallel. In this apparatus, by specifically constructing a multi-axis magnetic immersion objective lens required a low coil excitation and overlapping it with an electron deceleration, a multi-axis electromagnetic compound objective is formed to generate lower aberrations and lower radiation damage on specimen. Hence, this invention can provide a higher spatial resolution and a higher throughput than the previous prior arts mentioned above, which can especially benefit the wafer or mask defect inspection in semiconductor yield management. The descriptions below will focus on using a plurality of electron beams, and, however, it would be recognized that the invention has a much broader range of applicability.

Accordingly, a first embodiment of a multi-axis magnetic immersion objective lens is provided, which comprises a plurality of magnetic sub-lenses and a magnetic stage for mounting the specimen. Different from prior embodiment of the Chen et al. reference shown in FIG. 2C, a magnetic shielding plate with a plurality of circular openings is inserted between the upper magnetic plate (41) and the magnetic shielding tubes (16, 26, 36) above the upper magnetic plate (41), and called as upper magnetic shielding plate. Secondly, the upper and lower pole-pieces in each magnetic sub-lens are shaped to form a radial magnetic circuit gap. To match this formation, the upper and lower pole-pieces are respectively renamed as inner and outer pole-pieces in this invention. Through the radial magnetic circuit gap in each magnetic sub-lens, a stronger immersion magnetic field is provided on the specimen surface, which can focus an electron beam with lower aberrations. The magnetic specimen stage enhances the magnetic field of each sub-lens and moves its peak closer to the specimen. The first function of this design reduces the common coil excitation required to focus each electron beam. Therefore, the heat cooling is not necessary even when using a shorter working distance, which makes it possible to avoid additionally increasing complexity and instability of the system. A shorter working distance can reduce not only the basic aberrations (spherical and chromatic aberrations), but also the additional aberrations due to the residual non-axisymmetric transverse magnetic fields in front of the specimen. The second function of this design increases the magnetic field immersion on the specimen. It is well known that the stronger the immersion, the smaller the aberrations will be.

Based on the multi-axis magnetic immersion objective lens mentioned above, secondly, a multi-axis electrostatic immersion objective lens is added to generate a retarding field for deceleration of each electron beam. The multi-axis electrostatic immersion objective lens is constructed by all of the inner pole-pieces which are set at ground potential, the specimen which is set at a negative potential Vs, and a flat electrode plate which is set at a potential Ve equal to or higher than Vs. The flat electrode plate is located in the axial gap between the specimen and the inner pole-pieces, and has a plurality of circular orifices or through round holes, wherein each hole is aligned with an inner pole-piece. The multi-axis electrostatic immersion objective lens actually includes a plurality of electrostatic sub-lenses, wherein each is formed by the inner pole-piece, the flat electrode and the specimen, and therefore overlaps with a magnetic sub-lens in the multi-axis magnetic immersion objective lens. The retarding field generated by each electrostatic sub-lens can provide an effective way to reduce Coulomb effect and imaging aberrations at the same time. By being decelerated to a desired low landing energy just prior to impinging onto the specimen, the electron beam can pass through the remaining part of the electron optics with a higher energy so as to avoid suffering a strong Coulomb effect. The retarding field includes at least a negative electrostatic lens field. The negative aberrations generated by a negative electrostatic lens (divergent lens) can compensate most of the positive aberrations generated by a magnetic sub-lens. The combination of the multi-axis magnetic immersion objective lens and the multi-axis electrostatic immersion objective lens mentioned above is called as multi-axis electromagnetic compound immersion objective lens, and correspondingly a pair of magnetic sub-lens and electrostatic sub-lens overlapping with each other is called as an electromagnetic compound immersion objective sub-lens.

Based on the multi-axis electromagnetic compound immersion objective lens mentioned above, thirdly, a plurality of deflection scanning and compensation units can be added to scan a plurality of electron beams on the specimen surface and compensate the effect of the residual non-axisymmetric transverse field components. There is one deflection scanning and compensation unit inside each inner pole-piece, which includes two multi-pole lenses respectively located at the upper and lower ends of the inner pole-piece. Each of these two multi-pole lenses can act as a scanning deflector, a static deflector and a static stigmator at the same time. On the one hand, two scanning deflectors together operate as a deflection scanning unit to realize a close-to-lens-field deflection (or called as swing deflection) scanning which generates smaller off-axis aberrations. On the other hand, two static deflectors and two static stigmators operate as a compensation unit to cancel the effect of the residual magnetic dipole field and quadrupole field at the two ends of the inner pole-piece.

Therefore, this invention uses the combination of the multi-axis electromagnetic compound lens and a plurality of deflection scanning and compensation units mentioned above to construct an electron apparatus which uses a plurality of electron beams to inspect a specimen in parallel. An individual electron gun is located on the top of each electromagnetic compound immersion objective sub-lens, which generates an individual electron beam. An individual electrostatic condenser is located under each electron gun to focus the electron beam coming from the electron gun. An individual aperture is located under each condenser to limit the current of the electron beam coming from the condenser. A detector with a through round hole is located under each beam limit aperture. The electron beam passing through the hole of the detector then enters the following deflection scanning and compensation unit and electromagnetic compound immersion objective sub-lens. The electromagnetic compound immersion objective sub-lens focuses and decelerates the electron beam to be a low-voltage probe spot on the specimen surface, and the deflection scanning unit of the deflection scanning and compensation unit scans it. Secondary electrons are emitted from the incident site of the probe spot on specimen surface, then pass through the electromagnetic compound immersion objective sub-lens and deflection scanning and compensation unit and finally most of them land on the detector. The space from each electron gun to the top end of each magnetic sub-lens is magnetically shielded by four individual magnetic tubes. Counting from bottom to top, the first tube is stacked on the upper magnetic shielding plate of the multi-axis magnetic immersion objective lens to shield the space from the top end of the magnetic sub-lens to the detector. The second tube is located above the first tube with an axial space gap to shield the space from the beam limit aperture to the vacuum gate valve which separates the gun and the column. The space gap is designed for installing and replacing the detector and beam limit aperture when operating routine maintenance. The third tube is located above the second tube with an axial space gap to shield the space from the gun to the vacuum gate valve. The space gap is designed for installing the vacuum gate valve. The fourth tube is located to overlap with the top end of the third tube from inside, which is especially designed to fully cover the gun tip. A small deviation of an electron trajectory generated by the residual dipole field in the area near the gun tip will be magnified by the following system to a big landing position deviation on the specimen surface. To eliminate the non-axisymmetric transverse magnetic fields in all of the space gaps between the adjacent magnetic tubes, all of the magnetic tubes are covered by a larger common magnetic tube and a larger magnetic shielding plate on the top of the apparatus.

The flat electrode plate in the multi-axis electrostatic immersion objective lens can be either a larger single plate with a plurality of orifices or through holes respectively aligned with each inner pole-piece, or includes a plurality of small independent plates with a plurality of central holes respectively aligned with every inner pole-piece.

According to previous description, this invention provides a multi-axis magnetic immersion objective lens, which includes a pair of parallel magnetic conductor plates with a plurality of through round holes in pairs therein, a plurality of magnetic rings in pairs inside and aligned with the plurality of through round holes with a plurality of first radial gaps in pairs respectively, and a common excitation coil between the pair of the magnetic conductor plates for providing magnetic flux to the plurality of magnetic rings. The pair of parallel magnetic conductor plates includes an upper plate and a lower plate, wherein for each paired through round holes, an upper through round hole in the upper plate aligned with the corresponding lower through round hole in the lower plate. For each pair of magnetic rings in the pair of magnetic conductor plates respectively, an upper magnetic ring is aligned with and extends downward through inside the corresponding lower magnetic ring with a second radial gap. Each paired first radial gaps include a first upper radial gap between inner sidewall of the upper through round hole and outer sidewall of the upper magnetic ring, and a first lower radial gap between inner sidewall of the lower through round hole and outer sidewall of the lower magnetic ring. A plurality of magnetic sub-lens modules is therefore formed for focusing a plurality of charged particle beams respectively, wherein for each sub-lens module, the upper magnetic ring functions as an inner pole-piece and the corresponding lower magnetic ring functions as an outer pole-piece.

Each first and second radial gap can be either vacuum or filled with non-magnetic material. For each sub-lens module, the sizes of the first upper and lower radial gaps are smaller than the size of the second radial gap. For each sub-lens module, the first upper and lower radial gaps may have equal size or unequal sizes.

A specimen can be located below the pair of parallel magnetic conductor plates. The multi-axis magnetic immersion objective lens can further comprise a magnetic stage located below the specimen to sustain the specimen thereon, wherein the magnetic stage magnetically couples with the inner and outer pole-pieces of each sub-lens to create a strong magnetic field immersion to the specimen. Bottom ends of each pair of the inner and outer pole-pieces have equal distance to a surface of the specimen.

The multi-axis magnetic immersion objective lens may further comprise an upper magnetic shielding plate located above the pair of parallel magnetic conductor plates, and a lower magnetic shielding plate located below the pair of parallel magnetic conductor plates. The upper and lower magnetic shielding plates have a plurality of circular openings aligned with the plurality of through round holes respectively. A top end of the each inner pole-piece extends upward to inside each circular opening in the upper magnetic shielding plate with the upper radial gap, and stops at or below a top surface of the upper magnetic shielding plate. Each circular opening in the upper magnetic shielding plate may have a shape of upside-down counterbore. A top end of each inner pole-piece extends upward to inside a lower portion of the each upside-down counterbore without touching inner wall thereof, and has an inner diameter equal to or larger than an inner diameter of the upper portion of the upside-down counterbore. Bottom ends of each pair of the inner and outer pole-pieces extend downward to inside each circular opening in the lower magnetic shielding plate with the first lower radial gap and stop at or above a bottom surface of the lower magnetic shielding plate. The each magnetic sub-lens module includes a first working distance between a bottom end of the inner pole-piece and a surface of the specimen, and a second working distance between a bottom end of the outer pole-piece and the surface of the specimen. The first working distance can be shorter than the second working distance.

For the plurality of sub-lens modules, the second radial gaps can be unequal to each other, or identical to each other. The plurality of first radial gaps may have sizes increasing with a distance from each first radial gap to a corresponding geometric central axis of the pair of parallel magnetic conductor plates. For the plurality of through round holes, the holes located on the central portion of the pair of parallel magnetic conductor plates may have inner diameters smaller than those located on the peripheral portion of the pair of parallel magnetic conductor plates. For the plurality of inner and outer pole-pieces, the pole-pieces located on the central portion of the pair of parallel magnetic conductor plates may have outer diameters larger than those located on the peripheral portion of the pair of parallel magnetic conductor plates. The plurality of first radial gaps may have equal size with the distance from each first radial gap to a corresponding geometric central axis of the pair of parallel magnetic conductor plates. For each pair of magnetic rings, the upper magnetic ring has a cylindrical shape or funnel shape with narrow bottom end inside the corresponding lower magnetic ring.

This invention also provides a multi-axis electromagnetic compound immersion objective lens, which comprises the multi-axis magnetic immersion objective lens, an upper magnetic shielding plate located above the pair of parallel magnetic conductor plates, a lower magnetic shielding plate located below the pair of parallel magnetic conductor plates, a specimen located below the lower magnetic shielding plate, and a flat electrode located above the specimen and below the lower magnetic shielding plate with a plurality of circle orifices. A plurality of electrostatic sub-lens modules is therefore formed respectively and aligned with the plurality of magnetic sub-lens modules, wherein each electrostatic sub-lens module includes the inner pole-piece, the flat electrode and the specimen as a first electrode, a second electrode, and a third electrode respectively. The flat electrode can be divided into a plurality of individual segments, and each segment includes one of the plurality of circular orifices in the flat electrode. The upper and lower magnetic shielding plates have a plurality of circular openings aligned with the plurality of through round holes respectively. The plurality of circle orifices is respectively aligned with the plurality of openings in the lower magnetic shielding plate.

Each first and second radial gap can be vacuum or filled with non-magnetic material. For each magnetic sub-lens module, the sizes of the first upper and lower radial gaps can be smaller than the size of the second radial gap. For each sub-lens module, the first upper and lower radial gaps may have equal size. The multi-axis electromagnetic compound immersion objective lens may further comprise a magnetic stage located below the specimen to sustain the specimen thereon, wherein the magnetic stage magnetically couples with the inner and outer pole-pieces of each magnetic sub-lens to create a strong magnetic field immersion to the specimen.

Each circular opening in the upper magnetic shielding plate may have a shape of upside-down counterbore. A top end of each inner pole-piece extends upward to inside a lower portion of the each upside-down counterbore without touching inner wall thereof, and has an inner diameter equal to or larger than an inner diameter of the upper portion of the upside-down counterbore. Bottom ends of each pair of the inner and outer pole-pieces extend downward to inside each circular opening in the lower magnetic shielding plate with the lower radial gap and stop at or above a bottom surface of the lower magnetic shielding plate.

Each magnetic sub-lens module includes a first working distance between bottom end of the inner pole-piece and a surface of the specimen, and a second working distance between bottom end of the outer pole-piece and the surface of the specimen. The first working distance is shorter than the second working distance.

For the plurality of magnetic sub-lens modules, the second radial gaps can be identical to each other. The plurality of first radial gaps may have sizes increasing with a distance from each first radial gap to a corresponding geometric central axis of the pair of parallel magnetic conductor plates. For the plurality of through round holes, the holes located on the central portion of the pair of parallel magnetic conductor plates may have inner diameters smaller than those located on the peripheral portion of the pair of parallel magnetic conductor plates. For the plurality of inner and outer pole-pieces, the pole-pieces located on the central portion of the pair of parallel magnetic conductor plates have outer diameters larger than those located on the peripheral portion of the pair of parallel magnetic conductor plates. For each pair of magnetic rings, the upper magnetic ring has a cylindrical shape or funnel shape with narrow bottom end inside the corresponding lower magnetic ring.

This invention further provides a multi-axis charged particle apparatus, which comprises a multi-axis electromagnetic compound immersion objective lens, a plurality of deflection scanning and compensation units respectively located inside the plurality of magnetic sub-lens models in the multi-axis electromagnetic compound immersion objective lens, and a plurality of sub-columns located over the multi-axis electromagnetic compound immersion objective lens.

The multi-axis electromagnetic compound immersion objective lens comprises a multi-axis magnetic immersion objective lens, an upper magnetic shielding plate located above the pair of parallel magnetic conductor plates, a lower magnetic shielding plate located below the pair of parallel magnetic conductor plates, a specimen located below the lower magnetic shielding plate, and a plurality of flat electrodes located above the specimen and below the lower magnetic shielding plate with a plurality of circle orifices. The upper and lower magnetic shielding plates have a plurality of circular openings aligned with the plurality of through round holes respectively. The plurality of circle orifices are respectively aligned with the plurality of openings in the lower magnetic shielding plate. A plurality of electrostatic sub-lens modules is therefore formed respectively and aligned with the plurality of magnetic sub-lens modules, wherein each electrostatic sub-lens module includes the inner pole-piece, a flat electrode of the plurality of flat electrodes and the specimen as a first electrode, a second electrode, and a third electrode respectively.

Each of the plurality of deflection scanning and compensation unit comprises an upper electrostatic multi-pole lens located at an upper end of and aligned with the inner pole-piece, and generating a dipole field only, or a dipole field as well as a quadrupole field, and a lower electrostatic multi-pole lens located at a lower end of and aligned with the inner pole-piece, and generating a dipole field only or a dipole field and a quadrupole field. A deflection scanning unit is therefore formed to scan one of the plurality of charged particle beams on the specimen, and a compensation unit to compensate the influence of the dipole field and the quadrupole field generated by the multi-axis electromagnetic compound immersion objective lens.

Each of the plurality of sub-columns comprises a charged particle source for generating a charged particle beam, a condenser below the charged particle source for condensing the charged particle beam, a beam limit aperture below the condenser for confining the charged particle beam, a detector below the beam limit aperture for collecting a signal charged particle beam emanated from the specimen, a first magnetic shielding tube enclosing a first space between the detector and the upper magnetic shielding plate and aligned with an opening in the upper magnetic shielding plate, wherein a lower end of the first magnetic shielding tube stacks on a top surface of the upper magnetic shielding plate, a second magnetic shielding tube enclosing a second space between the condenser and the beam limit aperture, a third magnetic shielding tube enclosing the charged particle source and the condenser, a fourth magnetic shielding tube enclosing the charged particle source inside the third magnetic shielding tube, and a magnetic shielding house enclosing the plurality of sub-columns. The multi-axis charged particle apparatus may further comprise a fifth magnetic tube between the detector and the beam limit aperture.

The pair of parallel magnetic conductor plates, the plurality of magnetic rings, the upper magnetic shielding plate, the lower magnetic shielding plate, the first magnetic shielding tube, the second magnetic shielding tube, the third magnetic shielding tube, the fourth magnetic shielding tube, and the magnetic shielding house are set at ground potential. Each charged particle source is an electron source at a negative potential. The specimen and the magnetic stage are set at a negative potential higher than the potential of each electron source. Each flat electrode is set at a potential equal to or higher than the potential of the specimen. On the one hand, the plurality of flat electrodes can be set at same potential, and can be united to be a single large flat electrode which includes all of the circle orifices of the plurality of flat electrodes. On the other hand, the plurality of flat electrodes can be set at different potentials.

Each first and second radial gap can be vacuum or filled with non-magnetic material. For each magnetic sub-lens module, the sizes of the first upper and lower radial gaps can be smaller than the size of the second radial gap. For each magnetic sub-lens module, the first upper and lower radial gaps may have equal size. The multi-axis charged particle apparatus may further comprise a magnetic stage located below the specimen to sustain the specimen thereon, wherein the magnetic stage magnetically couples with the inner and outer pole-pieces of each magnetic sub-lens to create a strong magnetic field immersion to the specimen.

Each circular opening in the upper magnetic shielding plate may have a shape of upside-down counterbore. A top end of each inner pole-piece extends upward to inside a lower portion of the each upside-down counterbore without touching inner wall thereof, and has an inner diameter equal to or larger than an inner diameter of the upper portion of the upside-down counterbore. Bottom ends of each pair of the inner and outer pole-pieces extend downward to inside each circular opening in the lower magnetic shielding plate with the lower radial gap and stop at or above a bottom surface of the lower magnetic shielding plate. Each magnetic sub-lens module includes a first working distance between bottom end of the inner pole-piece and a surface of the specimen, and a second working distance between bottom end of the outer pole-piece and the surface of the specimen. The first working distance is shorter than the second working distance. For the plurality of magnetic sub-lens modules, the second radial gap can be identical to each other.

For the plurality of magnetic sub-lens modules, the first upper and lower radial gaps of the sub-lens modules located on a central portion of the pair of parallel magnetic conductor plates may have sizes smaller than those located on a peripheral portion of the pair of parallel magnetic conductor plates. For the plurality of through round holes, the holes located on the central portion of the pair of parallel magnetic conductor plates may have inner diameters smaller than those located on the peripheral portion of the pair of parallel magnetic conductor plates. For the plurality of inner and outer pole-pieces, the pole-pieces located on the central portion of the pair of parallel magnetic conductor plates may have outer diameters larger than those located on the peripheral portion of the pair of parallel magnetic conductor plates. For each pair of magnetic rings, the upper magnetic ring has a cylindrical shape or funnel shape whose narrow bottom end is inside the corresponding lower magnetic ring.

BRIEF DESCRIPTION OF THE DRAWINGS

The present invention will be readily understood by the following detailed description in conjunction with the accompanying drawings, wherein like reference numerals designate like structural elements, and in which.

DETAILED DESCRIPTION OF THE INVENTION

Figure 1A:
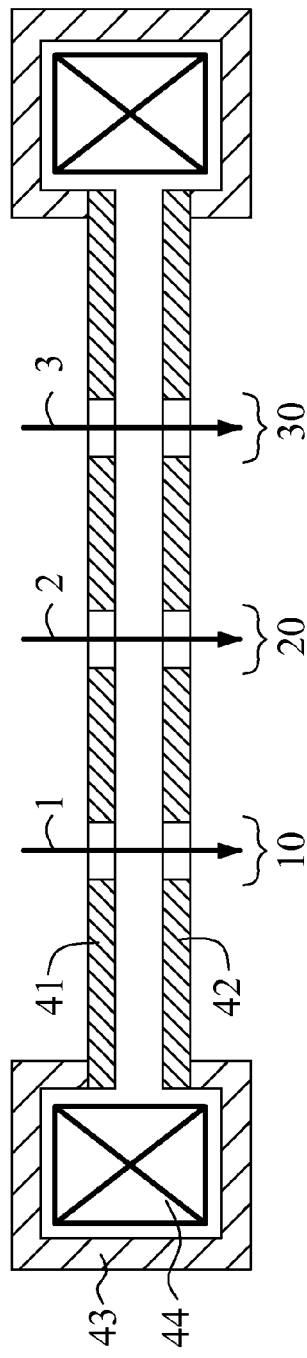
FIG. 1A is a schematic illustration of a conventional multi-axis magnetic lens.
Figure 1B:
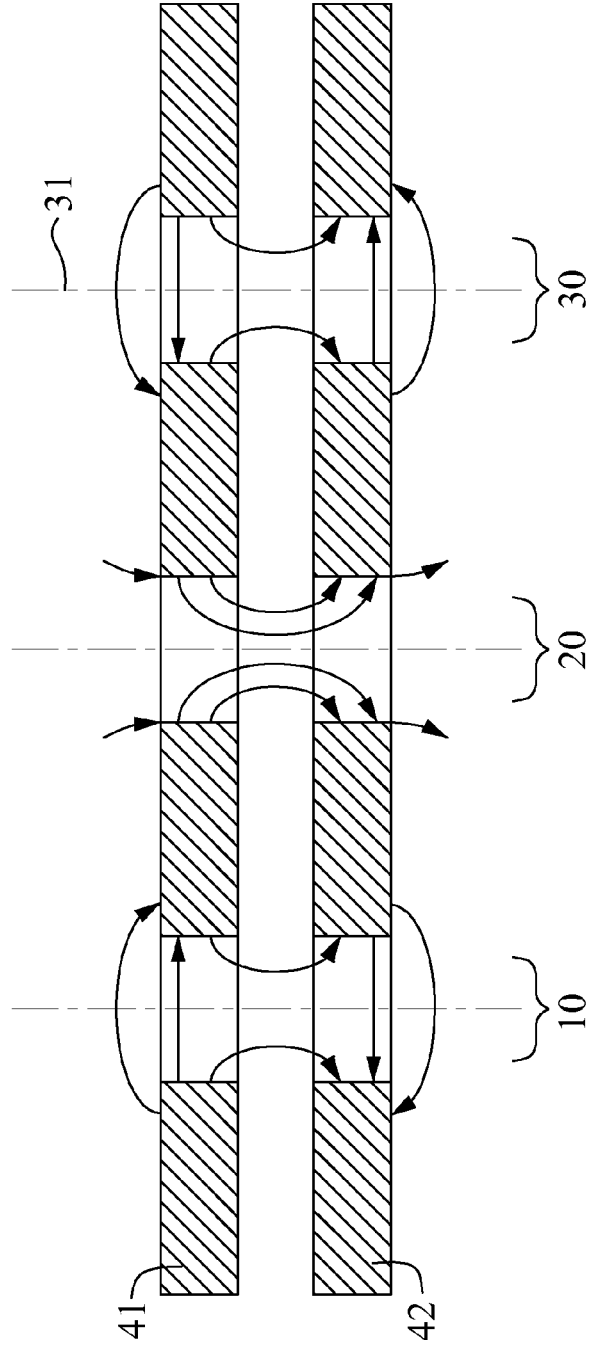
FIG. 1B is a schematic illustration of magnetic flux lines in FIG. 1A.
Figure 2A:
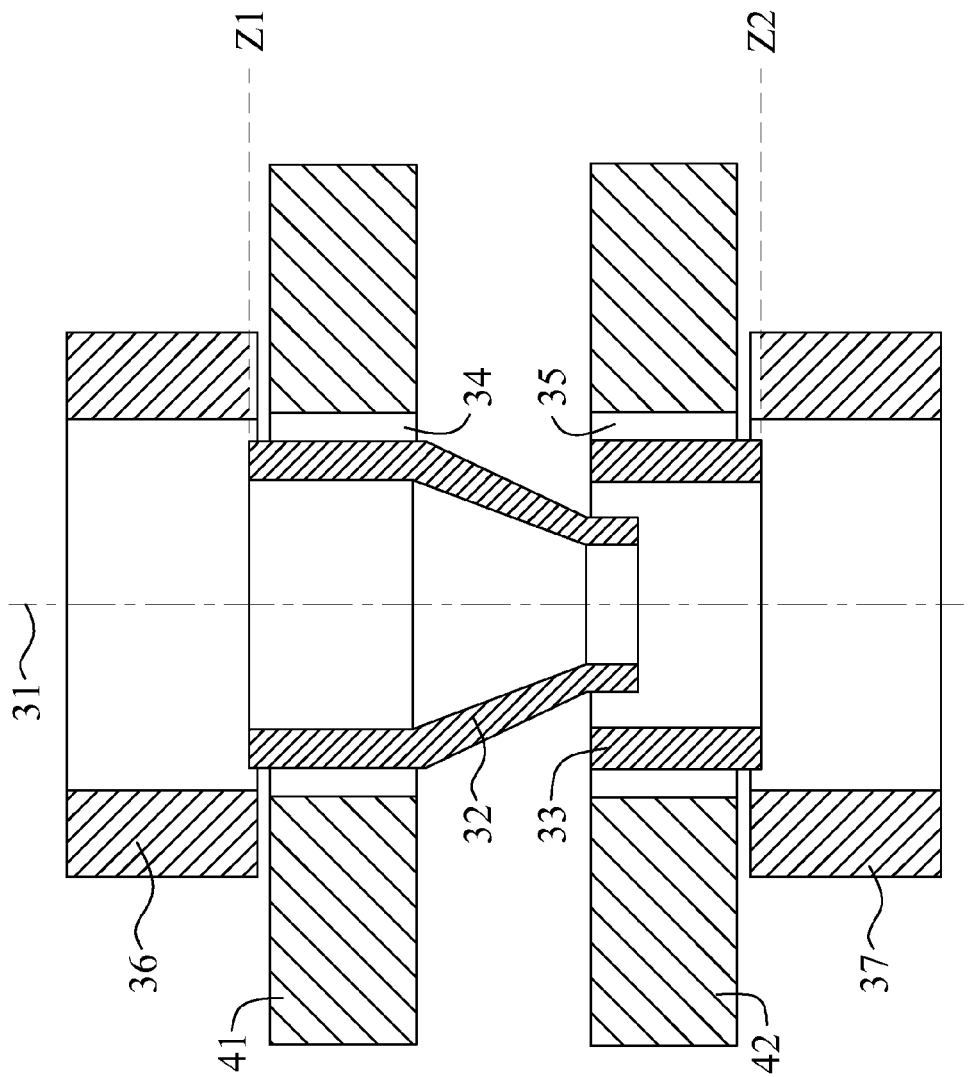
FIG. 2A is a schematic illustration of a sub-lens in a modified conventional multi-axis magnetic lens.
Figure 2B:
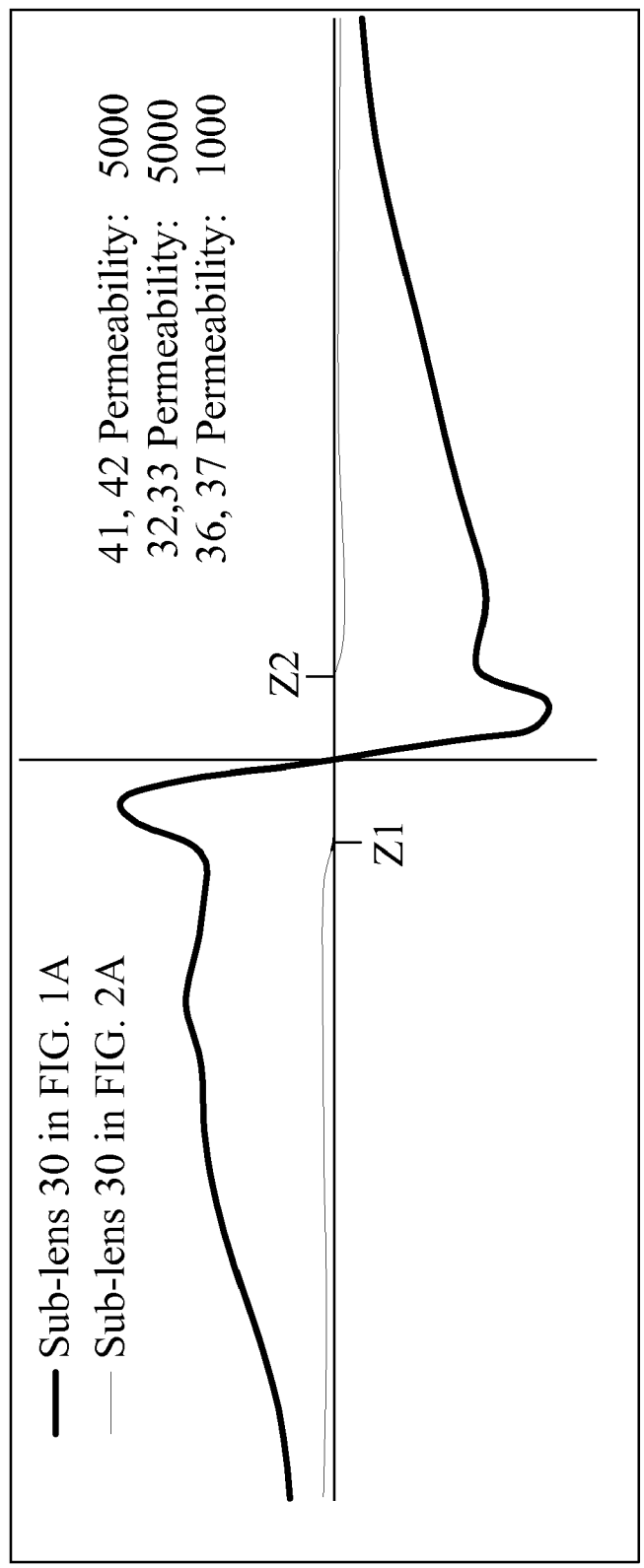
FIG. 2B is a schematic illustration of on-axis dipole field distribution of a sub-lens in FIG. 1A and FIG. 2A.
Figure 2C:
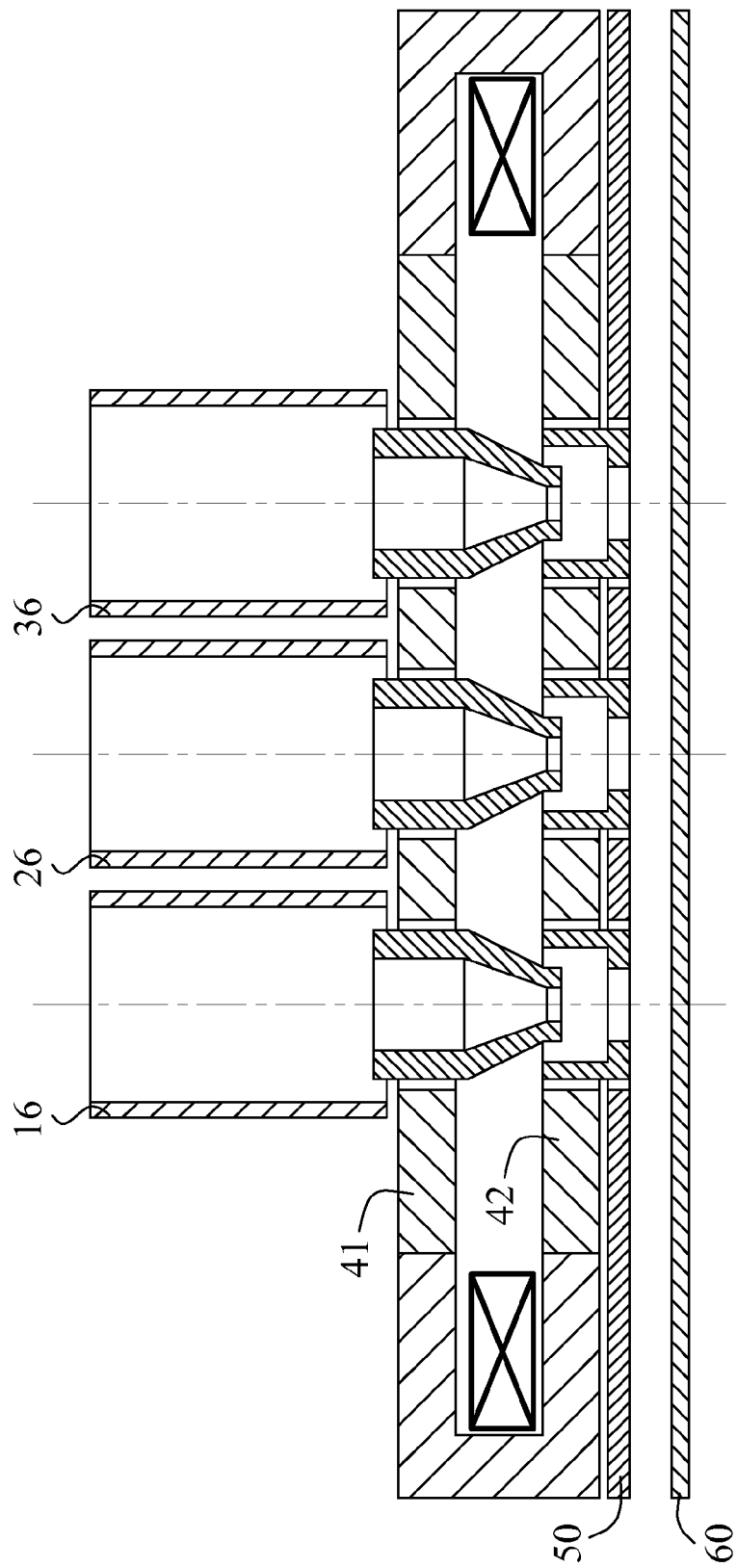
FIG. 2C is a schematic illustration of an example of FIG. 2A as a magnetic objective lens.

Reference will now be made in detail to specific embodiments of the invention. Examples of these embodiments are illustrated in accompanying drawings. While the invention will be described in conjunction with these specific embodiments, it will be understood that it is not intended to limit the invention to these embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations are not described in detail in order not to unnecessarily obscure the present invention.

In this invention, all terms relating to through round holes, circular openings, or circular orifices mean round openings or circular holes penetrated through one plate. Sometimes, especially through round holes always refer to holes in a magnetic conductor plate, circular openings always refer to holes in a magnetic shielding plate, and circular orifices always refer to holes in an electrode plate. Further, the term radial gap means two circular articles are concentric in which the radial gap is between the two circular articles.

The present invention provides an apparatus employing a multi-axis magnetic lens and LVSEM (low-voltage scanning electron microscope) technology, that uses a plurality of low-energy charged particle beams to inspect a specimen in parallel. In this apparatus, by specifically constructing a multi-axis magnetic immersion objective lens required a low coil excitation and overlapping it with a charged particle deceleration, a multi-axis electromagnetic compound immersion objective is formed to generate lower aberrations and lower radiation damage on specimen. A multi-axis charged particle apparatus is also provided in this invention by using the multi-axis electromagnetic immersion objective lens. Hence, this invention can provide a higher spatial resolution and a higher throughput than the previous patents mentioned above, which can especially benefit the wafer or mask defect inspection in semiconductor yield management. The descriptions below will focus on using a plurality of electron beams, which are a kind of charged particles. However, it would be recognized that the invention has a much broader range of applicability. For example, a plurality of electron beams can be applied to E-beam inspection tool, or E-beam lithography, while charge particle other than electrons, such as ion beams, can be applied to FIB (Focused Ion Beam).

The multi-axis magnetic lens provided in this invention includes a pair of parallel magnetic conductor plates with a plurality of through round holes in pairs therein, a plurality of magnetic rings in pairs inside and aligned with the plurality of through round holes with a plurality of first radial gaps in pairs respectively, and a common excitation coil between the pair of the magnetic conductor plates for providing magnetic flux to the plurality of magnetic rings. The plurality of through round holes in pairs means one through round hole in one plate of the pair of magnetic conductor plates will correspond to the other through round hole in the other plate of the pair of magnetic conductor plates. The plurality of magnetic rings in pairs means a magnetic ring in one through round hole in one plate of the pair of magnetic conductor plates and the other magnetic ring in the other through round hole in the other plate of the pair of magnetic conductor plates.

The pair of magnetic conductor plates includes an upper plate and a lower plate, wherein for each paired through round holes, an upper through round hole in the upper plate aligned with the corresponding lower through round hole in the lower plate.

For each pair of magnetic rings in the pair of magnetic conductor plates respectively, an upper magnetic ring is aligned with and extends downward through inside the corresponding lower magnetic ring with a second radial gap. Each paired first radial gaps include a first upper radial gap between inner sidewall of the upper through round hole and outer sidewall of the upper magnetic ring, and a first lower radial gap between inner sidewall of the lower through round hole and outer sidewall of the lower magnetic ring. For each sub-lens module, sizes of the first upper and lower radial gaps are smaller than the size of the second radial gap. The first upper and lower radial gaps can have equal size or unequal sizes. The first radial gaps and second radial gaps can be vacuum or filled with non-magnetic material. For the plurality of sub-lens modules, the second radial gaps can be unequal to each other or identical with each other.

A plurality of magnetic sub-lens modules is therefore formed for focusing a plurality of charged particle beams respectively, wherein for each sub-lens module, the upper magnetic ring functions as an inner pole-piece and the corresponding lower magnetic ring functions as an outer pole-piece. The inner pole-piece may have a cylindrical shape or funnel shape with narrow bottom end inside the corresponding outer pole-piece.

The multi-axis magnetic lens further includes a york to enclose the common excitation coil and to connect to the pair of magnetic conductor plates.

The multi-axis magnetic lens further includes a magnetic stage to sustain a specimen thereon, where the magnetic stage is under the lower plate. The magnetic stage will magnetically couple with the inner pole-piece and out pole-piece of each sub-lens module to create a strong magnetic field immersion to the specimen.

The multi-axis magnetic lens further includes an upper magnetic shielding plate over the upper plate and a lower magnetic shielding plate under the lower plate. Each of the upper magnetic shielding plate and the lower magnetic shielding plate has a plurality of circular openings aligned with the plurality of through round holes respectively. For each sub-lens module, a top end of the inner pole-piece can extend upward to inside of a circular opening in the upper magnetic shielding plate with the first upper radial gaps, and stop at or below a top surface of the upper magnetic shielding plate. Each circular opening in the upper magnetic shielding plate can have an upside-down counterbore, and the top end of the inner pole-piece can extend upward to inside a lower portion of each upside-down counterbore without touching inner wall of it, in which an inner diameter of the inner pole-piece is equal to or larger than the upper portion of the upside-down counterbore. For each sub-lens module, bottom ends of the inner pole-piece and outer pole-piece can extend downward to inside the circular opening in the lower magnetic shielding plate with the first radial gap, and stop at or above a bottom surface of the lower magnetic shielding plate.

A first working distance is defined between a bottom end of the inner pole-piece and specimen surface, and a second working distance is defined between a bottom end of the outer pole-piece and specimen surface. The first working distance and the second working distance can be equal or unequal. In a preferred embodiment, the first working distance is shorter than the second working distance.

For the plurality of sub-lens modules, the plurality of first gaps can have size increasing with a distance from each first radial gap to a corresponding geometric central axis of the pair of magnetic conductor plates, and the through round holes located on the central portion of the pair of parallel magnetic conductor plates have inner diameters smaller than those located on the peripheral portion of the pair of parallel magnetic conductor plates.

The following will describe some embodiments of this invention with referring to drawings. Although all the discussions are based on a structure of one sub-lens for one electron beam, however, it would be recognized the present invention can be applied to a plurality of sub-lenses and has a much broader range of applicability. Although the number of sub-lens is free to increase, it is better to locate the new sub-lens with the least increasing of the geometric structure's asymmetry of the multi-axis magnetic objective lens.

Figure 3A:
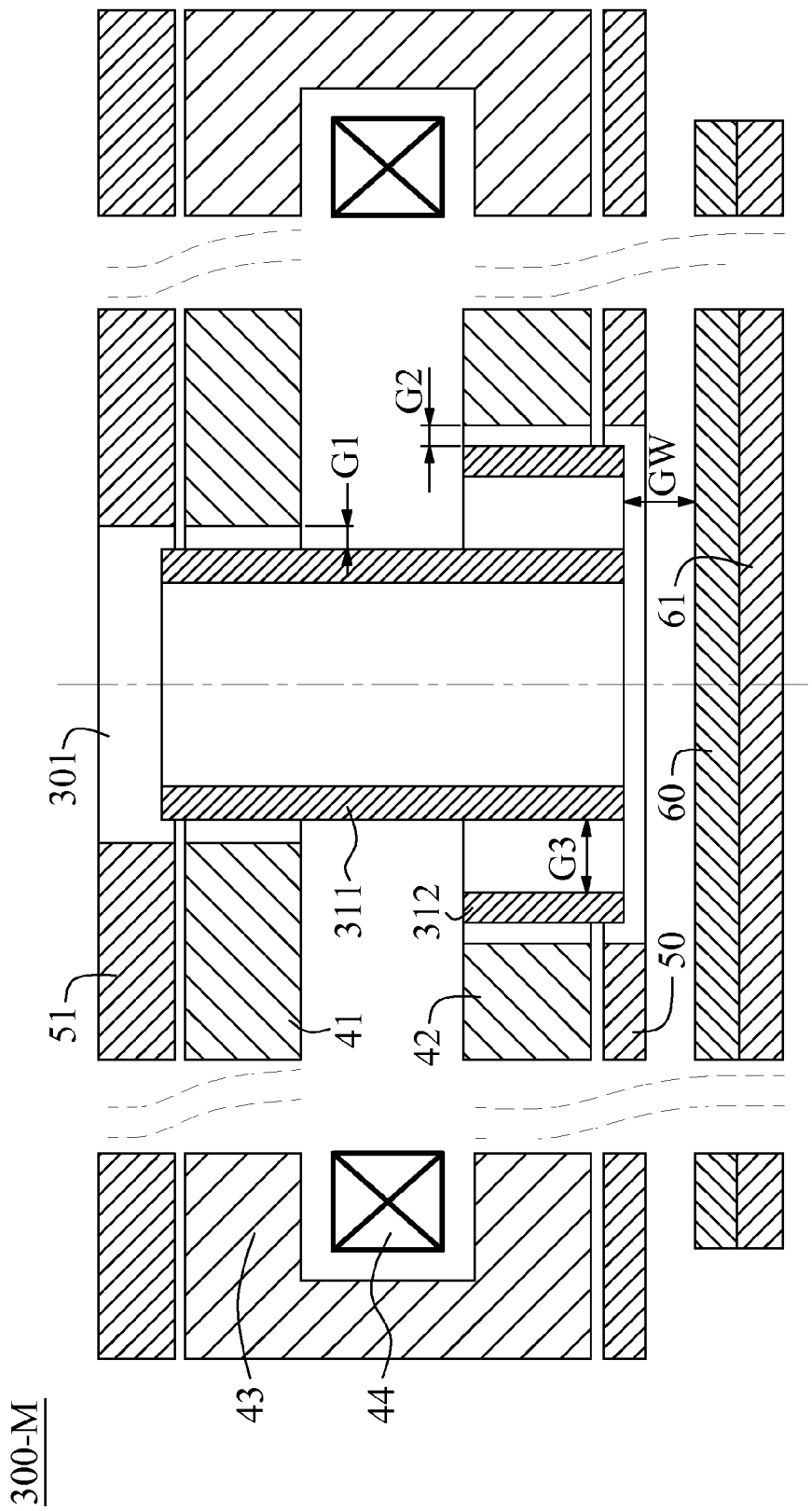
FIG. 3A to FIG. 3D are schematic illustrations of variant sub-lenses in a multi-axis magnetic immersion objective lens in accordance with a first embodiment of the present invention.

The multi-axis magnetic immersion objective lens in FIG. 3A includes one excitation coil 44, two magnetic plates 41 and 42, and a plurality of magnetic ring in pairs (311 plus 312) in the two magnetic plates 41 and 42 respectively. To explain it clearly, only one sub-lens named as 300-M is shown. The two magnetic plates 41 and 42, which includes an upper plate 41 and a lower plate 42, have a plurality of through round holes in pairs respectively, wherein for each paired through round holes as an example, as shown in FIG. 3A, an upper through round hole in the upper plate 41 is aligned with the corresponding lower through round hole in the lower plate 42. Although size of the upper through round holes in FIG. 3A is smaller than size of the lower through round hole, both the upper and lower through round holes can be the same. In a preferred embodiment, the lower through round hole has larger size compared to the upper through round hole.

A plurality of magnetic rings in pairs is configured in the plurality of through round holes respectively. For each paired magnetic rings, the two magnetic rings 311 and 312, which include an upper ring 311 and a corresponding lower ring 312, are configured in the upper through round hole and lower through round hole respectively with a first upper radial gap G1 and a first lower radial gap G2 respectively. Both the upper magnetic ring 311 and the lower magnetic ring 312, which are made of material with high permeability, are cylindrical in one embodiment, as shown in FIG. 3A. A sub-lens module is therefore formed by the excitation coil 44, two magnetic plates 41 and 42, the upper and lower through round holes, and the two magnetic rings 311 and 312, wherein the upper magnetic ring 311 functions as an inner pole-piece and the lower magnetic ring 312 functions as outer pole-piece. The excitation coil 44 provides magnetic flux to the inner pole-piece 311 and the outer pole-piece 312.

Please refer to FIG. 3A again, in which the multi-axis magnetic immersion objective lens further includes a coil york 43, and two magnetic shielding plates 50 and 51. The coil york 43 and the two magnetic plates 41 and 42 cover the coil 44 from side, top and bottom respectively. The two magnetic shielding plates 50 and 51 are optionally respectively located above the upper magnetic plate 41 with a non-magnetic gap and under the lower magnetic plate 42 with a non-magnetic gap. The specimen stage 61 is located under the lower magnetic shielding plate 50. There is a plurality of circular openings in each of the two plates 50 and 51 for electron beams passing through. Each through round hole or circular opening in one of these four plates 41, 42, 50 and 51 is aligned with three other holes and openings respectively in the remaining three plates.

The inner pole-piece 311 extends through and aligned with the holes in the upper and lower magnetic plates 41 and 42. In addition, its upper end can further extend upward inside the lower part of the circular opening in the upper magnetic shielding plate 51 as shown in FIG. 3A, and its lower end further extends downward inside the circular opening in the lower magnetic shielding plate 50. The outer pole-piece 312 extends through the hole in the lower magnetic plate 42 from outside of the inner pole-piece 311 and is aligned with the inner pole-piece 311. Its lower end further extends inside the circular opening in the lower magnetic shielding plate 50. The pole-piece 311 and 312 do not touch the inner sidewall of every hole, and the space gaps are either vacuum or filled with a non-magnetic material.

The length of axial space gap GW between the inner pole-piece 311 and a surface of the specimen 60 is equal to a distance between the outer pole-piece 312 and the surface of the specimen 60. If the coil 44 is excited by a current, a magnetic round lens field is provided through the radial magnetic circuit gap G3 between each pair of inner and outer pole-pieces 311 and 312. Hence, it is said that each pair of inner and outer pole-pieces 311 and 312 forms a radial-gap magnetic sub-lens, and in this invention a plurality of sub-lenses can be formed although in FIG. 3A only one sub-lens is shown. As conventionally, the length of axial gap GW between the inner pole-piece 311 and the specimen 60 is called as working distance of a magnetic sub-lens. There is a plurality of such magnetic sub-lens, and all are excited by a common coil 44.

One magnetic sub-lens will be used to focus an electron beam to a probe spot on the specimen surface 60 for specimen inspection. Due to the radial gap G3 between the inner pole-piece 311 and the outer pole-piece 312, the magnetic sub-lens can provide a very strong magnetic field immersion on the specimen surface, and hence the probe spot has small aberrations.

Please refer to FIG. 3A again, in which the multi-axis magnetic immersion objective lens further includes a magnetic specimen stage 61. Compared with conventionally using a non-magnetic specimen stage, using a magnetic specimen stage can further enhance the magnetic round lens field of each sub-lens and move the magnetic field peak of each sub-lens closer to the specimen. Consequently, at first, the common coil excitation required to focus each electron beam is reduced, which solves the conventional concern that a radial-gap magnetic lens needs a larger coil excitation. Therefore, an extra cooling device for removing exhausting heat is not necessary even when using a short working distance which usually requires a larger coil excitation. This design avoids additionally increasing complexity and instability of the system. Secondly, a short working distance can be used without increasing much coil excitation. Using a short working distance reduces the focal length of a sub-lens and shortens the operation range of the residual non-axisymmetric transverse magnetic fields in front of the specimen. As a result, it reduces the basic axisymmetric aberrations (spherical and chromatic aberrations) and the additional non-axisymmetric aberrations at the same time. Thirdly, the magnetic field immersion on the specimen is increased because the magnetic field peak is closer to the specimen. It is well known that the stronger the immersion, the smaller the aberrations will be.

Figure 3B:
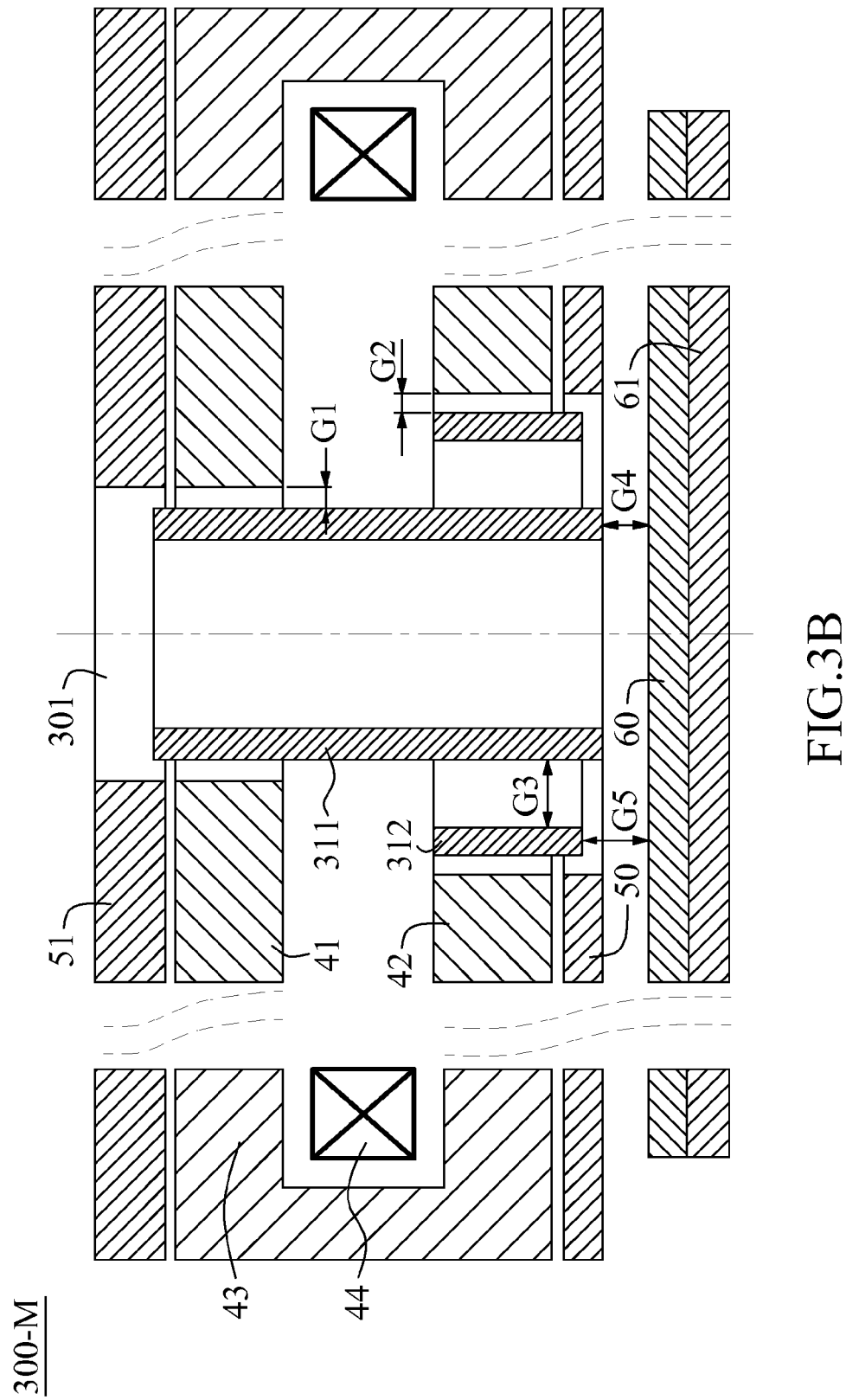

Please refer to FIG. 3B, in which another embodiment of the multi-axis magnetic immersion objective lens is provided. In this embodiment, distance G4 between surface of the specimen 60 and the lower end of the inner pole-piece 311 is shorter than distance G5 between surface of the specimen 60 and the lower end of the outer pole-piece 312. In this configuration, magnetic field provided by the inner pole-piece 311 can further enhance magnetic field immersion on the specimen 60.

Figure 3C:
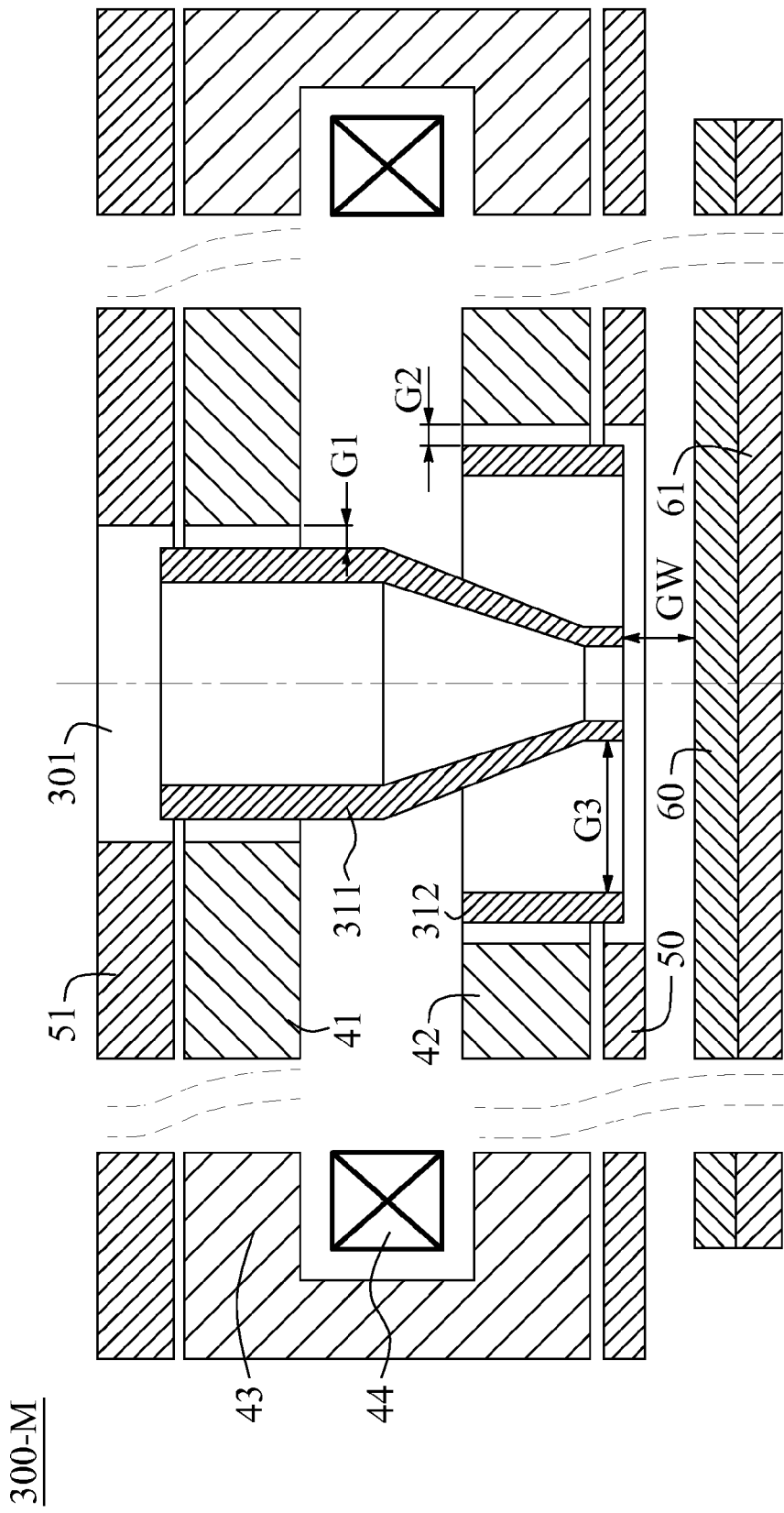

Please refer to FIG. 3C, in which still another embodiment of the multi-axis magnetic immersion objective lens is provided. In this embodiment, the inner pole-piece 311 has a funnel outline that can reduce the magnetic coupling between the inner pole-piece 311 and the outer pole-piece 312, and make more magnetic flux leak out though the radial magnetic circuit gap G3 at the lower ends of inner pole-piece 311 and outer pole-piece 312. This makes this embodiment need a coil excitation smaller than the previous two embodiments.

Figure 3D:
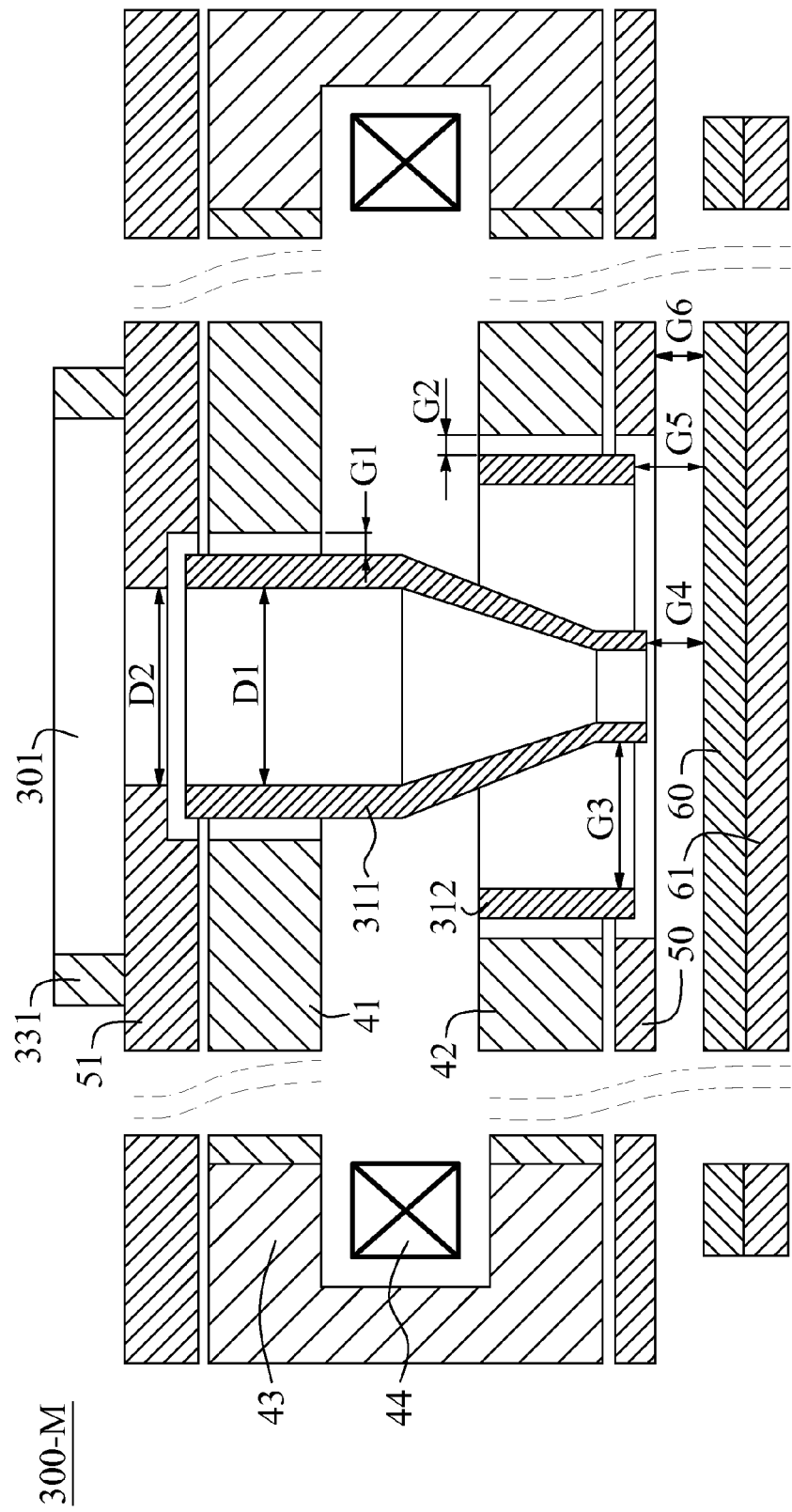

FIG. 3D shows a structure of a preferred embodiment of a multi-axis magnetic immersion objective lens according to the present invention. To explain it clearly, only one sub-lens named as 300-M is shown. The magnetic rings 311 and 312, or respectively called as inner pole-piece 311 and outer pole-piece 312, extend through the holes in the upper and lower magnetic plates 41 and 42 with a radial gap G1 and G2 respectively. The space inside G1 and G2 can be a vacuum or filled with a non-magnetic material. The thickness of the radial gap G1 and G2 are chosen by taking account of the residual of the non-axisymmetric transverse field components and the coil excitation. The thinner the gap, the stronger the non-axisymmetric transverse field components will be left. The thicker the gap, the higher the excitation of the coil 44 will be required. The lower end of the inner pole-piece 311 extends inside the outer pole-piece 312. The lower ends of inner pole-piece 311 and outer pole-piece 312 extend inside the hole in the lower shielding magnetic plate 50 and forms a radial magnetic circuit gap G3, which can be vacuum or filled with non-magnetic material. The upper end of the inner pole-piece 311 extends inside the lower part of the upside-down counterbore shape hole in the upper shielding plate 51, and has an inner diameter D1 nearly equal to the inner diameter D2 of the upper part of that hole.

The specimen 60 is mounted on the magnetic stage 61. The length of the axial gap G4 between specimen 60 and inner pole-piece 311 is called as working distance of sub-lens 300-M. Both of the axial gap G5 between specimen 60 and outer pole-piece 312 and the axial gap G4 are longer than the axial gap G6 between specimen 60 and lower shielding magnetic plate 50. The axial gaps G4 and G5 are not necessarily to have same length. It depends on the required orientation of the magnetic circuit gap G3. When G4 is a little shorter than G5, the gap G3 is turned to face away from the optical axis 301 and a deeper magnetic immersion is provided. The common coil 44 provides a magnetic round lens field through the gap G3, the magnetic stage 61 further enhances this field and makes its peak further closer to the surface of the specimen 60. Therefore, the specimen 60 can be immersed in a strong magnetic field. This strong immersion magnetic field reduces the aberrations of sub-lens 300-M to a great degree. The enhancement of the magnetic field by the magnetic stage 61 reduces the coil excitation required for focusing an electron beam, thereafter removes the cooling requirement for the common coil. As a result, it avoids increasing complexity and instability of the system. The design of magnetic stage 61 makes using a short working distance G4 possible, because usually a short working distance requires a high coil excitation which will generate more heat. A shorter working distance can reduce not only the basic aberrations (spherical and chromatic aberrations), but also the additional aberrations due to the residual non-axisymmetric transverse magnetic fields in front of the specimen. Although the multi-axis electromagnetic immersion objective lens has a non-axisymmetric structure, each sub-lens within it is axisymmetrical about the sub-lens optical axis.

In this embodiment, the magnetic shielding plate 51 has an upside down counterbore with a smaller diameter D2 to shield magnetic field from the inner pole-piece 311. Further, a tube 331 stacked on the magnetic shielding plate 51 to shield the magnetic flux leaked out from the portions of the magnetic shielding plate 51 outside this sub-lens.

To realize a low radiation damage on specimen, the electron beam must land on the specimen surface with a low energy. It is well known that the lower the electron beam energy, the stronger the Coulomb effect will be. To reduce the Coulomb effect as much as possible, electron deceleration or called as retarding is employed. The electron beam is initially accelerated to a high kinetic energy and subsequently decelerated to a desired low final landing energy just prior to impinging onto the specimen. This is realized by combining a multi-axis electrostatic immersion objective lens with the multi-axis magnetic immersion objective lens mentioned above. The multi-axis electrostatic immersion objective lens includes a plurality of electrostatic sub-lenses. Each electrostatic sub-lens is overlapped with each magnetic sub-lens in the multi-axis magnetic immersion objective lens, so as to provide an electrostatic retarding field to decelerate the electron beam passing through them.

An electrostatic sub-lens is formed by the inner pole-piece of a magnetic sub-lens, the specimen and a flat electrode located between the specimen and the inner pole-piece. The flat electrode can be an individual plate with a circle orifice or through round hole aligned with inner pole-piece, or a single plate with a plurality of circle orifices or through round holes, wherein each hole is aligned with each inner pole-piece. In an electrostatic sub-lens, the inner pole-piece are set at ground potential, the specimen is set at a negative potential Vs, and the flat electrode plate is set at a potential Ve equal to or higher than Vs. The retarding field generated by each electrostatic sub-lens can provide an effective way to reduce Coulomb effect and imaging aberrations at the same time. For example, after being emitted from a cathode at a negative potential Vc which is much lower than the specimen potential Vs, the electrons can be accelerated to a higher energy |e·Vc| immediately, then keep this energy when passing through the following system, and finally be decelerated by the retarding field to a desired low landing energy |e·(Vs−Vc)| just prior to impinging onto the specimen. It is well known that the higher the electron energy, the weaker the Coulomb Effect is.

The retarding field includes at least a negative electrostatic lens field. The negative aberrations generated by a negative electrostatic lens (divergent lens) can compensate most of the positive aberrations generated by a magnetic sub-lens. The combination of the multi-axis magnetic immersion objective lens and the multi-axis electrostatic immersion objective lens is called as multi-axis electromagnetic compound immersion objective lens, and the combination of a pair of magnetic sub-lens and electrostatic sub-lens overlapping with each other is called as an electromagnetic compound immersion objective sub-lens.

This invention then provides a multi-axis electromagnetic compound immersion objective lens, which comprises a multi-axis magnetic immersion objective lens, an upper magnetic shielding plate located above the pair of parallel magnetic conductor plates, a lower magnetic shielding plate located below the pair of parallel magnetic conductor plates, a specimen located below the lower magnetic shielding plate, and a flat electrode located above the specimen and below the lower magnetic shielding plate with a plurality of circle orifices. A plurality of electrostatic sub-lens modules is therefore formed respectively and aligned with the plurality of magnetic sub-lens modules, wherein each electrostatic sub-lens module includes the inner pole-piece, the flat electrode and the specimen as a first electrode, a second electrode, and a third electrode respectively. The flat electrode can be divided into a plurality of individual segments, and each segment includes one of the plurality of circle orifices in the flat electrode. The upper and lower magnetic shielding plates have a plurality of circular openings aligned with the plurality of through round holes respectively. The plurality of circle orifices is respectively aligned with the plurality of openings in the lower magnetic shielding plate.

The following will describe some embodiments of this invention with referring to drawings. Although all the discussions are based on a structure of one sub-lens for one electron beam, however, it would be recognized the present invention can be applied to a plurality of sub-lenses and has a much broader range of applicability. Although the number of sub-lens is free to increase, it is better to locate the new sub-lens with the least increasing of the geometric structure's asymmetry of the multi-axis magnetic objective lens.

Figure 4:
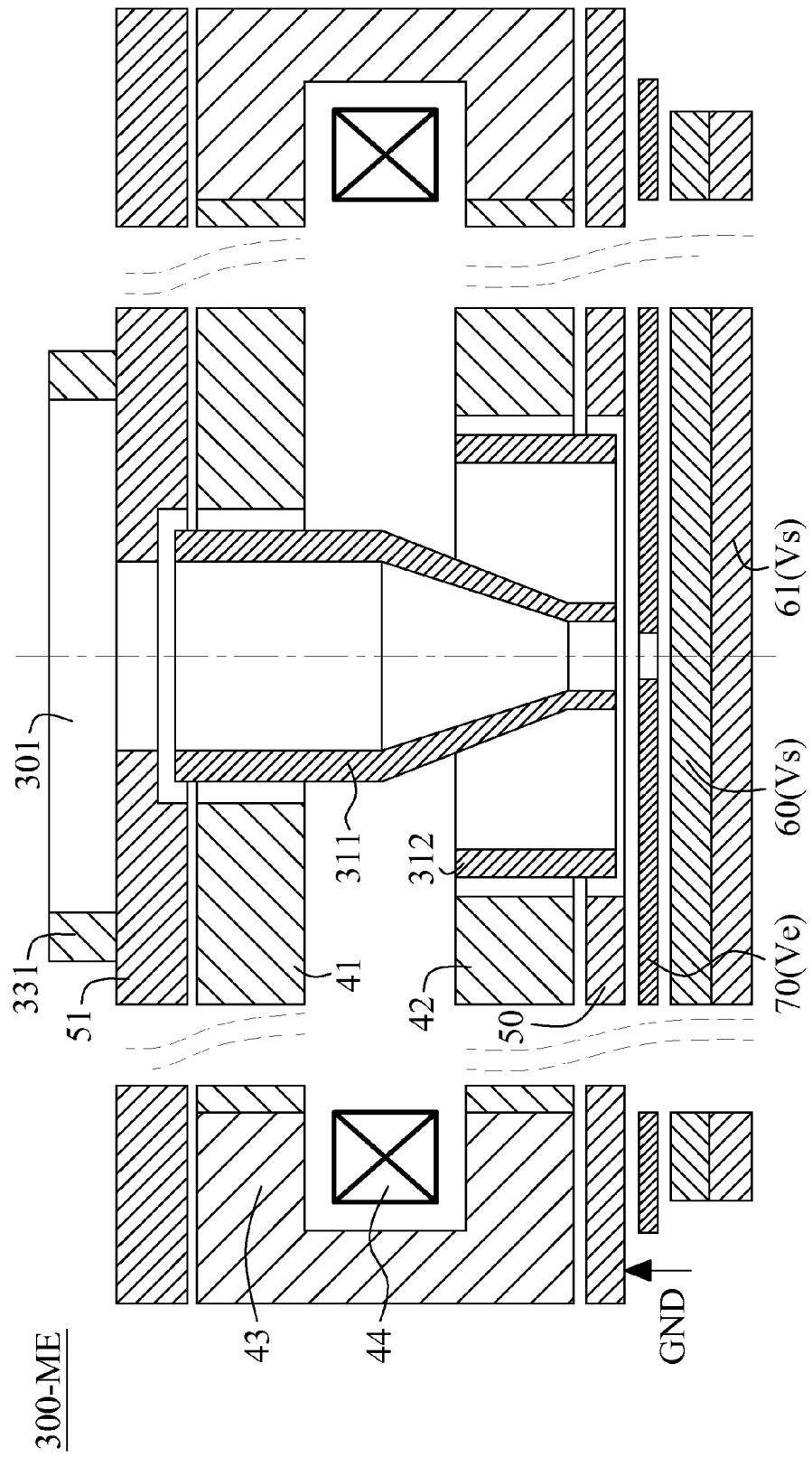
FIG. 4 is a schematic illustration of a sub-lens in a multi-axis electromagnetic compound immersion objective lens in accordance with a second embodiment of the present invention.

FIG. 4 shows a structure of an embodiment of a multi-axis electromagnetic compound immersion objective lens according to the present invention. To explain it clearly, only one sub-lens named as 300-ME is shown. A flat electrode 70 with a circular orifice or through round hole is inserted between the specimen 60, the lower shielding plate 50 and the inner pole-piece 311, wherein the inner diameter of the orifice or hole is equal to or little different from the inner diameter of the inner pole-piece 311. Except the magnetic stage 61, all of the magnetic elements (41, 42, 50, 51, 311, 312, 331) are set at ground potential. The specimen 60 and the magnetic stage 61 are set at a negative potential Vs, and the flat electrode 70 is set at a potential Ve equal to or higher than Vs. In this way a retarding field is generated in front of the specimen 60, and an electron beam can be decelerated just prior to impinging onto the specimen. The retarding method reduces the radiation damage on the specimen without obviously increasing Coulomb effect. The retarding field includes at least one negative electrostatic lens field. The negative aberrations generated by the negative electrostatic lens (divergent lens) can compensate most of the positive aberrations generated by pure magnetic sub-lens 300-M. Hence, the aberration coefficients of the electromagnetic compound sub-lens 300-ME are reduced to be 10~20% of those of the pure magnetic sub-lens 300-M.

To realize scanning a plurality of electron beams on the specimen in parallel, a plurality of deflection scanning units can be added to the multi-axis electromagnetic compound immersion objective lens mentioned above. Each deflection scanning unit is inserted inside the inner pole-piece in each electromagnetic compound immersion objective sub-lens. Each deflection scanning unit includes two deflectors, respectively located at the upper and lower ends of the inner-pole-piece. Both operate as a group to realize a close-to-lens-field deflection (or called as swing deflection) scanning which generates smaller off-axis aberrations. If the effect of the residual magnetic dipole fields at the two ends of the inner pole-piece is obviously degrade the quality of the electron beam landing on the specimen, these two deflectors can additionally be used to cancel the effect. In addition, if the effect of the residual magnetic quadrupole field at the two ends of the inner pole-piece is obviously degrade the quality of the electron beam landing on the specimen, these two deflectors can be constructed having multi-pole structure so as to be able to operate as deflector and stigmator at the same time, wherein these two stigmators can be used to cancel the effect. In these two cases mentioned above, a deflection scanning unit can be generally renamed as deflection scanning and compensation unit.

Figure 5:
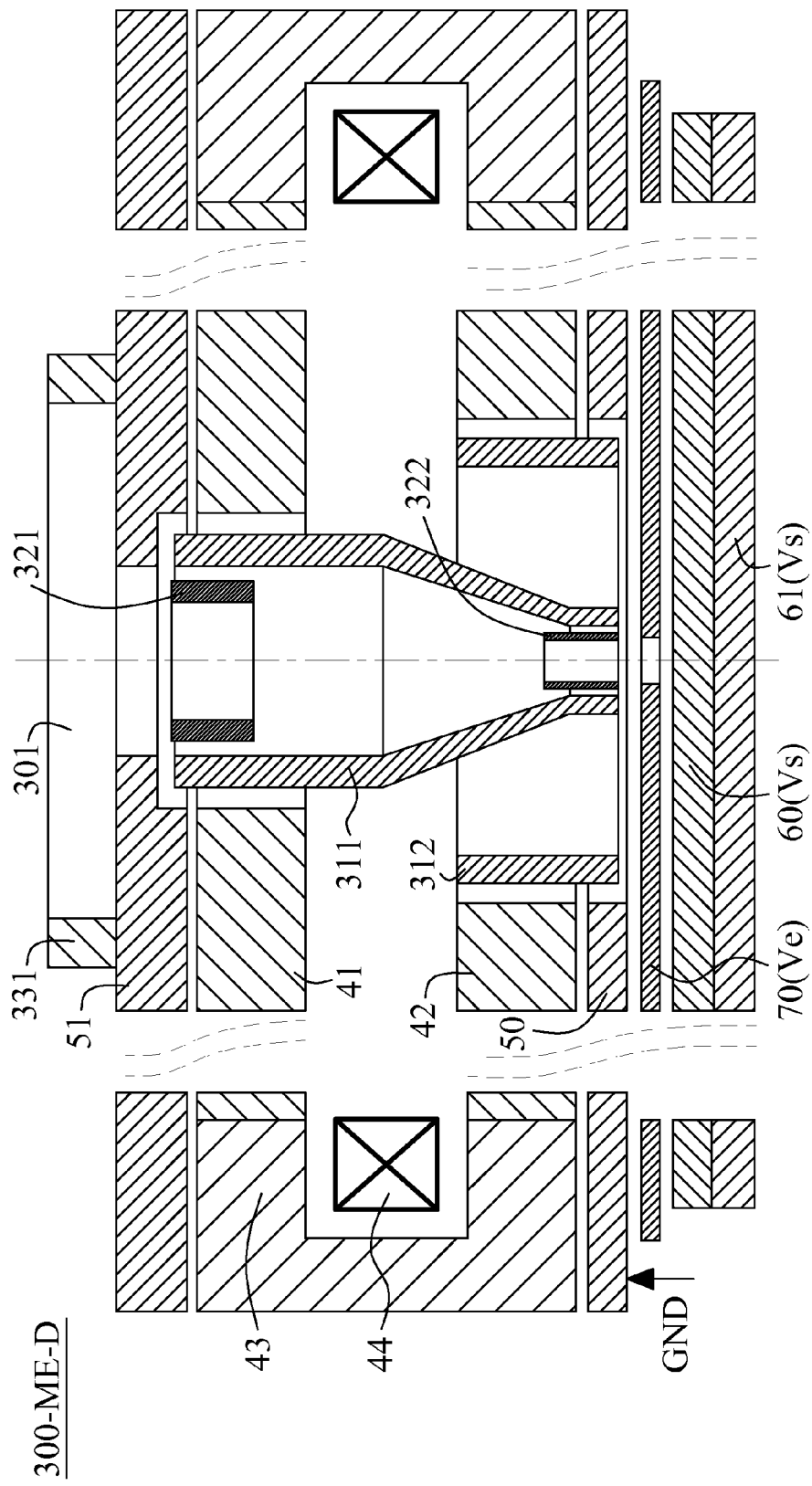
FIG. 5 is a schematic illustration of a sub-lens and a deflection scanning and compensation unit in a multi-axis electromagnetic compound immersion objective lens in accordance with a third embodiment of the present invention.

FIG. 5 shows a structure of an embodiment of a multi-axis electromagnetic compound immersion objective lens with a plurality of deflection scanning units according to the present invention. To explain it clearly, only one sub-lens 300-ME-D is shown. A pair of electrostatic deflectors 321 and 322 is inserted inside the bore of the inner pole-piece 311. The No. 1 deflector 321 is located near the upper end of 311, and the No. 2 deflector 322 is located near the lower end of 311. The two deflectors 321 and 322 operate together as a deflection scanning unit to scan the electron beam passing through 300-ME on the surface of the specimen 60. Because the deflection field generated by No. 2 deflector 322 is very close to the magnetic round lens field of the sub-lens 300-ME, the deflection scanning generates smaller off-axis aberrations. This makes it possible to use a large field of view when inspecting the specimen 60. Moreover, the two deflectors 321 and 322 can also be used to directly compensate the influence of the residual magnetic dipole field at the two ends of the inner pole-piece 311. The deflectors 321 and 322 can also be designed to have a multi-pole structure which can work as quadrupole lens as well as a dipole lens. In this case, 321 and 322 can also be used to directly compensate the influence of the residual magnetic quadrupole field at the two ends of the inner pole-piece 311. Because the compensation happens where the residual magnetic dipole and/or quadrupole field exists, the compensation effect will be very effective.

Figure 6A:
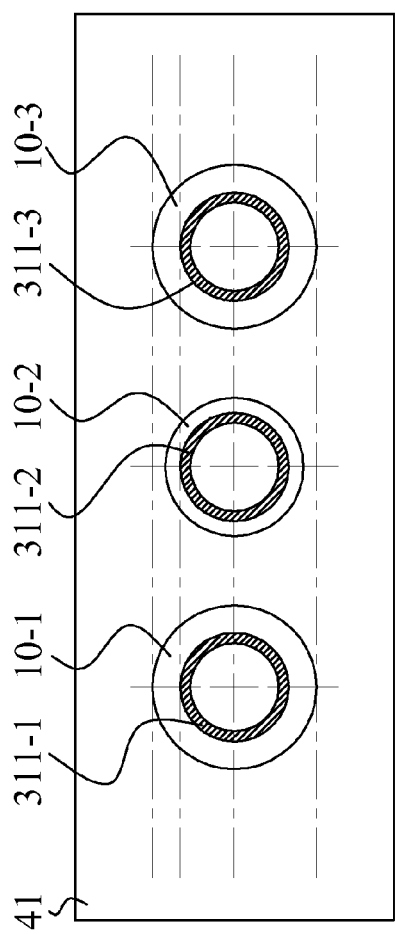
FIG. 6A and FIG. 6B are schematic top illustrations of three sub-lenses with different sizes in a multi-axis electromagnetic compound immersion objective lens in accordance with another embodiment of the present invention.
Figure 6B:
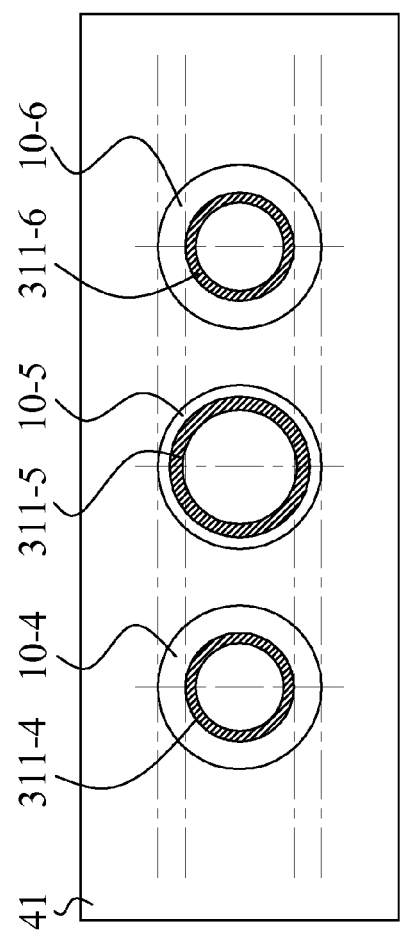

FIG. 6A and FIG. 6B illustrate different first radial gaps may vary among different sub-lens modules. Although all first radial gaps can be identical, however a preferred embodiment is radial gap in central sub-lens would be shorter than other radial gaps in peripheral sub-lens modules. To achieve this purpose, one way is that central through round hole 10-2 in the upper plate 41, as shown in FIG. 6A, can be shrunk directly compared to neighbor through round holes 10-1 and 10-3. It is noted that the central magnetic ring 311-2 has the same size compared to other peripheral magnetic rings 311-1 and 311-3. Another way is to enlarge central magnetic ring 311-5, as shown in FIG. 6B, while the peripheral magnetic rings 311-4 and 311-6 keep the same size. It is noted that all through round holes 10-4, 10-5, and 10-6 are all identical in the upper plate 41 in FIG. 6B. However, there is still some other way to shrink the central through round hole and enlarge central magnetic ring simultaneously and keep peripheral through round holes as well as magnetic rings constant.

Further, an apparatus of using a plurality of electron beams to inspect a specimen in parallel is constructed by using a multi-axis electromagnetic compound immersion objective lens and a plurality of close-to-lens-field deflection scanning units mentioned above. Each electromagnetic compound immersion objective sub-lens in the multi-axis electromagnetic compound immersion objective lens is combined with a close-to-lens-field deflection scanning unit, and the combination is called as a focusing and scanning sub-unit.

On the top area of each focusing and scanning sub-unit, from top to bottom, there is an individual electron gun, an individual electrostatic condenser, a beam limit aperture and a detector. An electron beam is generated by the electron gun and weakly focused by the condenser. The beam limit aperture confines the current of the electron beam by cutting off the electrons with larger polar angles. The detector has a center through round hole, so that the electron beam can pass through and enter the following focusing and scanning sub-unit. The focusing and scanning sub-unit focuses the electron beam to be a low-voltage probe spot on the specimen surface and scans it. Secondary electrons are emitted from the incident site of the probe spot on specimen surface, then pass through the focusing and scanning sub-unit and finally most of them land on the detector.

To reduce the non-axisymmetric transverse magnetic fields in the path of each electron beam as much as possible, the space from each electron gun to the top end of each magnetic sub-lens is magnetically shielded by four individual magnetic tubes. Counting from bottom to top, the first tube is stacked on the upper magnetic shielding plate of the multi-axis magnetic objective lens to shield the space from the top end of the sub-lens to the detector. The second tube is located above the first tube with an axial space gap to shield the space from the beam limit aperture to the vacuum gate valve which separates the gun and the column. The space gap is designed for installing and replacing the detector and beam limit aperture when operating routine maintenance. The third tube is located above the second tube with an axial space gap to shield the space from the gun to the vacuum gate valve. The space gap is designed for installing the vacuum gate valve. The fourth tube is located to overlap with the top end of the third tube from inside, which is especially designed to fully cover the gun tip. A small deviation of an electron trajectory generated by the residual dipole field in the area near the gun tip will be magnified by the following system to a big landing position deviation on the specimen surface. To eliminate the non-axisymmetric transverse magnetic fields in all of the space gaps between the adjacent magnetic tubes, all of the magnetic tubes are covered by a larger common magnetic tube and a larger magnetic shielding plate on the top of the apparatus.

This invention thus provides a multi-axis charged particle apparatus, which comprises a multi-axis electromagnetic compound immersion objective lens, a plurality of deflection scanning and compensation units respectively located inside the plurality of magnetic sub-lens models in the multi-axis electromagnetic compound immersion objective lens, and a plurality of sub-columns located over the multi-axis electromagnetic compound immersion objective lens.

The multi-axis electromagnetic compound immersion objective lens comprises a multi-axis magnetic immersion objective lens, an upper magnetic shielding plate located above the pair of parallel magnetic conductor plates, a lower magnetic shielding plate located below the pair of parallel magnetic conductor plates, a specimen located below the lower magnetic shielding plate, and a plurality of flat electrodes located above the specimen and below the lower magnetic shielding plate with a plurality of circle orifices. The upper and lower magnetic shielding plates have a plurality of circular openings aligned with the plurality of through round holes respectively. The plurality of circle orifices are respectively aligned with the plurality of openings in the lower magnetic shielding plate. A plurality of electrostatic sub-lens modules is therefore formed respectively and aligned with the plurality of magnetic sub-lens modules, wherein each electrostatic sub-lens module includes the inner pole-piece, a flat electrode of the plurality of flat electrodes and the specimen as a first electrode, a second electrode, and a third electrode respectively.

Each of the plurality of deflection scanning and compensation unit comprises an upper electrostatic multi-pole lens located at an upper end of and aligned with the inner pole-piece, and generating a dipole field only, or a dipole field as well as a quadrupole field, and a lower electrostatic multi-pole lens located at a lower end of and aligned with the inner pole-piece, and generating a dipole field only or a dipole field and a quadrupole field. A deflection scanning unit is therefore formed to scan one of the plurality of charged particle beams on the specimen, and a compensation unit to compensate the influence of the dipole field and the quadrupole field generated by the multi-axis electromagnetic compound immersion objective lens.

Each of the plurality of sub-columns comprises a charged particle source for generating a charged particle beam, a condenser below the charged particle source for condensing the charged particle beam, a beam limit aperture below the condenser for confining the charged particle beam, a detector below the beam limit aperture for collecting a signal charged particle beam emanated from the specimen, a first magnetic shielding tube enclosing a first space between the detector and the upper magnetic shielding plate and aligned with an opening in the upper magnetic shielding plate, wherein a lower end of the first magnetic shielding tube stacks on a top surface of the upper magnetic shielding plate, a second magnetic shielding tube enclosing a second space between the condenser and the beam limit aperture, a third magnetic shielding tube enclosing the charged particle source and the condenser, a fourth magnetic shielding tube enclosing the charged particle source inside the third magnetic shielding tube, and a magnetic shielding house enclosing the plurality of sub-columns. The multi-axis charged particle apparatus may further comprise a fifth magnetic tube between the detector and the beam limit aperture.

The pair of parallel magnetic conductor plates, the plurality of magnetic rings, the upper magnetic shielding plate, the lower magnetic shielding plate, the first magnetic shielding tube, the second magnetic shielding tube, the third magnetic shielding tube, the fourth magnetic shielding tube, and the magnetic shielding house are set at ground potential.

Each charged particle source is an electron source at a negative potential. The specimen and the magnetic stage are set at a negative potential higher than the potential of each electron source. Each flat electrode is set at a potential equal to or higher than the potential of the specimen. On the one hand, the plurality of flat electrodes can be set at same potential, and can be united to be a single large flat electrode which includes all of the circle orifices of the plurality of flat electrodes. On the other hand, the plurality of flat electrodes can be set at different potentials.

The following will describe some embodiments of this invention with referring to drawings. Although all the discussions are based on a structure of 3 sub-lenses for three electron beams, however, it would be recognized the present invention can be applied to more than three sub-lenses and has a much broader range of applicability. Although the number of sub-lens is free to increase, it is better to locate the new sub-lens with the least increasing of the geometric structure's asymmetry of the multi-axis magnetic objective lens.

Figure 7:
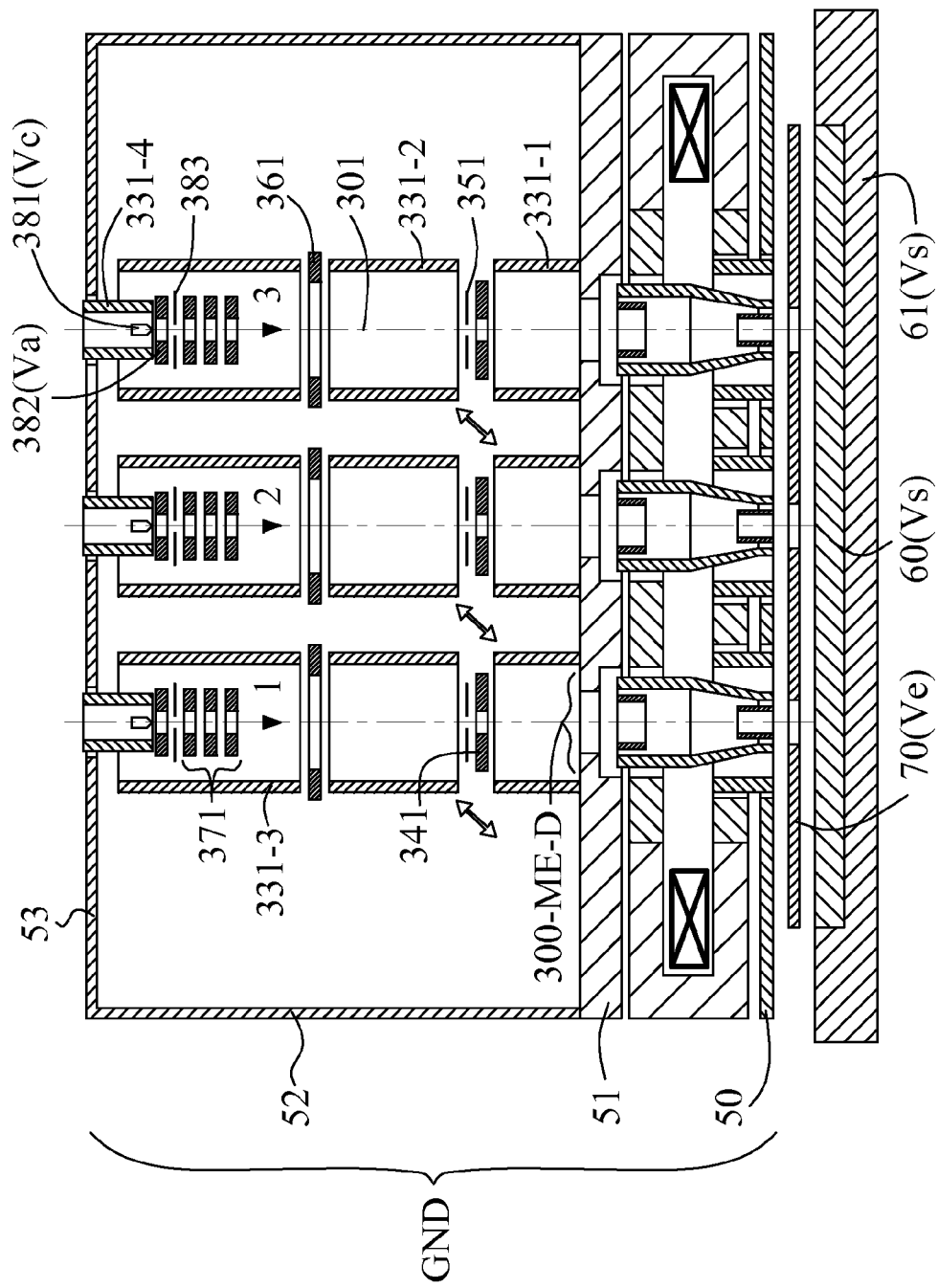
FIG. 7 is a schematic illustration of a multi-axis charged particle apparatus in accordance with an embodiment of the present invention.

FIG. 7 shows an embodiment of an apparatus using a plurality of electron beams to inspect a specimen in parallel according to the present invention. The apparatus is constructed based on a multi-axis electromagnetic compound immersion objective lens combined with a plurality of deflection scanning units. To explain it clearly, only a case with three beams is shown as an example. Three electron beams 1~3 are emitted respectively by three individual cathodes. Beam 3 is taken as an example to describe the structure. When cathode 381 is at negative potential Vc and the anode 382 is at a specific potential Va higher than Vc, the electron beam 3 is emitted. The gun aperture 383 is at ground potential, and cut the current of the electron beam 3 to be just larger then the maximum probe current for inspecting specimen. The electrostatic condenser 371 weakly focuses the beam 3 and control the current of the beam 3 passing through the beam limit aperture 351. The beam 3 passes through the center hole of the detector 341, and then enters into the sub-lens 300-ME-D.

The specimen 60 and the magnetic specimen stage 61 are at negative potential Vs which is higher than the potential Vc of the cathode 381. Vs is set to ensure the landing energy |e·(Vs−Vc)| of the beam 3 to be a low energy such as <5 keV. The flat electrode 70 is at a potential Ve which is equal to or higher than Vs. The potential difference Ve−Vs is set to control the electrostatic field over the entire surface of the specimen 60 weaker than a permissible value for the specimen safety. The sub-lens 300-ME-D focuses, scans and decelerates the beam 3 onto the surface of the specimen 60. The spot of the beam 3 on the surface of the specimen 60 is called as probe spot. Secondary electrons are emitted from the incident site of the probe spot 3 on specimen surface, then pass through the sub-lens 300-ME-D and finally most of them land on the detector 341.

To reduce the non-axisymmetric transverse magnetic fields in the path of beam 3 from the cathode 381 to the shielding plate 51, four magnetic tubes 331-1~331-4 are located along the path. The first tube 331-1 is stacked on the upper shielding plate 51. The space between the first tube 331-1 and second tubes 331-2 is designed for installing and replacing the detector 341 and beam limit aperture 351 during routine preventive maintenance process. The space between the second tube 331-2 and third tubes 331-3 is designed for installing the vacuum gate valve 361. The fourth tube 331-4 is especially designed to fully cover the cathode 381. A small electron trajectory deviation generated by the residual dipole field in the area near the electron gun will be magnified by the following column, and finally adds larger additional aberrations to the size and position of the probe spot on the surface of the specimen 60. To eliminate the non-axisymmetric transverse magnetic fields in the space gaps between the magnetic tubes 331-1~331-4. All of the magnetic tubes are covered by a larger magnetic tube 52 and a top magnetic plate 53.

The flat electrode plate in the multi-axis electrostatic objective lens can be either a larger single plate with a plurality of through holes aligned with the inner pole-pieces, or includes a plurality of small independent plate which has a center hole aligned with an inner pole-piece.

Figure 8:
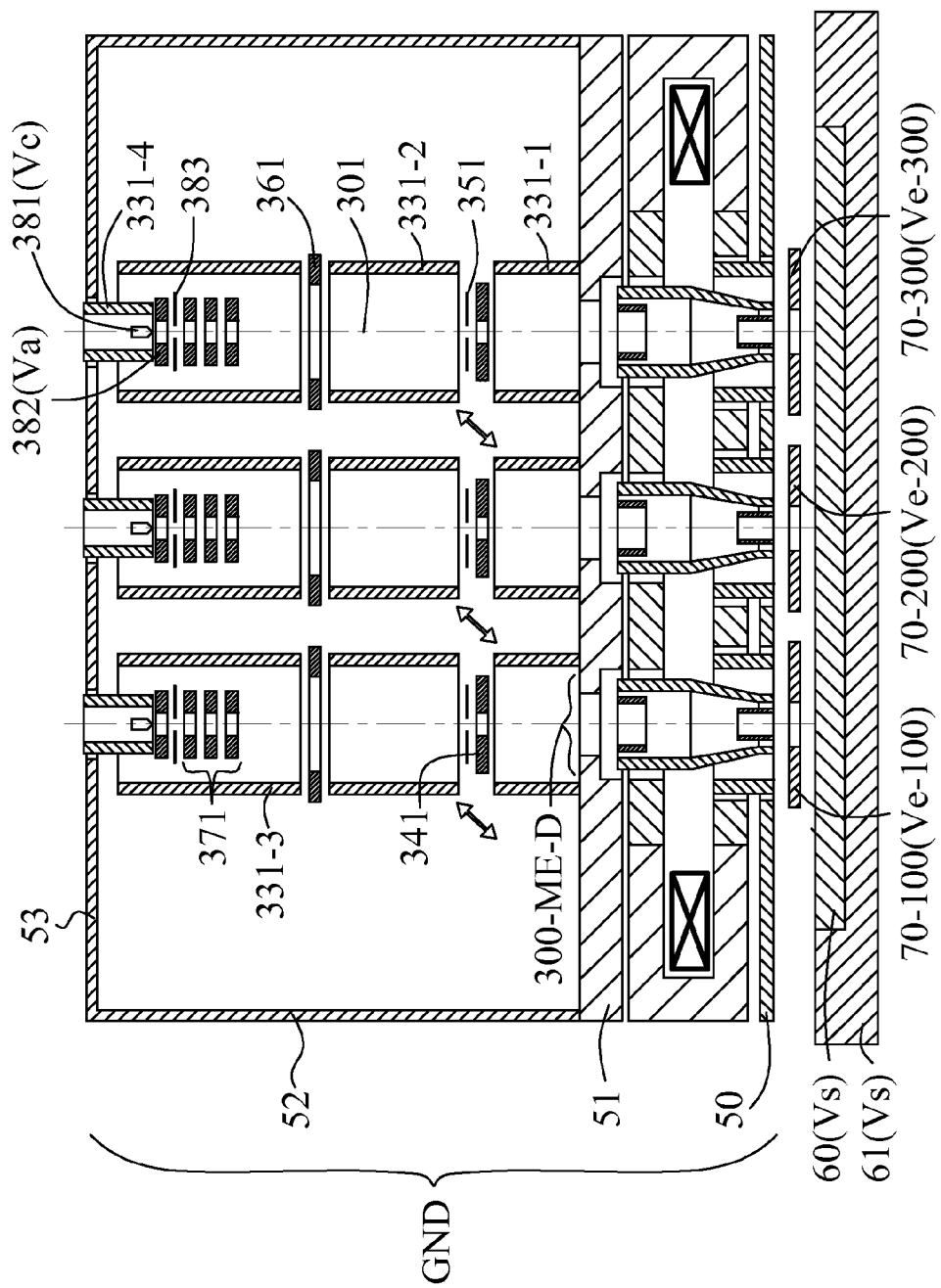
FIG. 8 is a schematic illustration of a multi-axis charged particle apparatus in accordance with another embodiment of the present invention.

FIG. 8 shows another embodiment of an apparatus using a plurality of electron beams to inspect a specimen in parallel according to the present invention. Different from the embodiment in FIG. 7, the large flat electrode 70 is replaced by three small flat electrodes 70-100, 70-200 and 70-300. The potentials of these three electrodes, Ve-100, Ve-200 and Ve-300 can be adjusted independently to compensate the fine focusing power difference among the three sub-lenses.

In this invention, at first a multi-axis magnetic immersion objective lens is provided, which comprises a plurality of magnetic sub-lenses with a radial magnetic circuit gap facing the specimen surface and a magnetic specimen stage. This design not only makes each sub-lens can focus a charged particle beam with lower aberrations, but also substantially reduces the common coil excitation so that the coil heat cooling is not necessary. Using a heat cooling unit will additionally increase complexity and instability of the objective lens. Secondly, a multi-axis electromagnetic compound immersion objective lens is provided, which comprises a multi-axis magnetic immersion objective lens mentioned above and a multi-axis electrostatic immersion objective lens which includes a plurality of electrostatic sub-lenses. Each electrostatic sub-lens generates a retarding field which makes it possible to realize inspecting the specimen with lower radiation damage and higher resolution at the same time. Thirdly, a plurality of deflection scanning and compensation units located inside a multi-axis electromagnetic compound immersion objective lens mentioned above is provided. Each unit acts as two deflectors and two stigmators at the same time to scan a focused particle beam on the specimen surface with lower off-axis aberrations and compensates the effect of the residual non-axisymmetric transverse field components in the magnetic sub-lens. Finally, an apparatus using a plurality of charged particle beams to inspect the specimen in parallel is provided, which employs a multi-axis electromagnetic compound immersion objective and a plurality of deflection scanning and compensation units mentioned above, a plurality of individual charged particle sources and a plurality of magnetic shielding units which wholly eliminate the non-axisymmetric transverse magnetic fields in the space from each charged particle source to the top end of the multi-axis electromagnetic compound immersion objective lens. Including all of the advantages mentioned above, the apparatus can consequently provide a higher spatial resolution and a higher throughput when inspecting a specimen, which can especially benefit the wafer or mask defect inspection in semiconductor yield management.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the invention as limited only by the appended claims.

What is claimed is:

1. A multi-axis charged particle apparatus, comprising:
a multi-axis electromagnetic compound immersion objective lens comprising:
a multi-axis magnetic immersion objective lens comprising:
a pair of parallel magnetic conductor plates with a plurality of through round holes in pairs therein, the pair of parallel magnetic conductor plates including an upper plate and a lower plate, for each paired through round holes, an upper through round hole in the upper plate aligned with a corresponding lower through round hole in the lower plate;
a plurality of magnetic rings in pairs inside and aligned with the plurality of through round holes with a plurality of first radial gaps in pairs respectively, wherein for each pair of magnetic rings in the pair of parallel magnetic conductor plates respectively, an upper magnetic ring is aligned with and extends downward through inside a corresponding lower magnetic ring with a second radial gap, wherein each paired first radial gaps include a first upper radial gap between inner sidewall of the upper through round hole and outer sidewall of the upper magnetic ring, and a first lower radial gap between inner sidewall of the lower through round hole and outer sidewall of the lower magnetic ring,
thereby forming a plurality of magnetic sub-lens modules for focusing a plurality of charged particle beams respectively, wherein for each sub-lens module, the upper magnetic ring functions as an inner pole-piece and the corresponding lower magnetic ring functions as an outer pole-piece; and
a common excitation coil located between the pair of parallel magnetic conductor plates for providing magnetic flux to the plurality of magnetic sub-lens modules;
an upper magnetic shielding plate located above the pair of parallel magnetic conductor plates;
a lower magnetic shielding plate located below the pair of parallel magnetic conductor plates, wherein the upper and lower magnetic shielding plates have a plurality of circular openings aligned with the plurality of through round holes respectively;
a specimen located below the lower magnetic shielding plate; and
a plurality of flat electrodes located above the specimen and below the lower magnetic shielding plate with a plurality of circle orifices, wherein the plurality of circle orifices are respectively aligned with the plurality of circular openings in the lower magnetic shielding plate,
thereby forming a plurality of electrostatic sub-lens modules respectively aligned with the plurality of magnetic sub-lens modules, wherein each electrostatic sub-lens module includes the inner pole-piece, a flat electrode of the plurality of flat electrodes and the specimen as a first electrode, a second electrode, and a third electrode respectively;
a plurality of deflection scanning and compensation units respectively located inside the plurality of magnetic sub-lens modules in the multi-axis electromagnetic compound immersion objective lens, wherein each of the plurality of deflection scanning and compensation units comprising:
an upper electrostatic multi-pole lens located at an upper end of and aligned with the inner pole-piece, and generating a dipole field only, or a dipole field as well as a quadrupole field; and
a lower electrostatic multi-pole lens located at a lower end of and aligned with the inner pole-piece, and generating a dipole field only or a dipole field and a quadrupole field,
thereby forming a deflection scanning unit to scan one of the plurality of charged particle beams on the specimen, and a compensation unit to compensate the influence of the dipole field and the quadrupole field generated by the multi-axis electromagnetic compound immersion objective lens; and
a plurality of sub-columns located over the multi-axis electromagnetic compound immersion objective lens, providing the plurality of charged particle beams, and aligned with the plurality of magnetic sub-lens modules respectively, wherein each of the plurality of sub-columns comprises:
- a charged particle source for generating a charged particle beam;
- a condenser below the charged particle source for condensing the charged particle beam;
- a beam limit aperture below the condenser for confining the charged particle beam;
- a detector below the beam limit aperture for collecting a signal charged particle beam emanated from the specimen;
- a first magnetic shielding tube enclosing a first space between the detector and the upper magnetic shielding plate and aligned with an opening in the upper magnetic shielding plate, wherein a lower end of the first magnetic shielding tube stacks on a top surface of the upper magnetic shielding plate;
- a second magnetic shielding tube enclosing a second space between the condenser and the beam limit aperture;
- a third magnetic shielding tube enclosing the charged particle source and the condenser;
- a fourth magnetic shielding tube enclosing the charged particle source inside the third magnetic shielding tube; and
- a magnetic shielding house enclosing the plurality of sub-columns.

2. The multi-axis charged particle apparatus according to claim 1, wherein each first and second radial gap is vacuum or filled with non-magnetic material.

3. The multi-axis charged particle apparatus according to claim 2, wherein for each magnetic sub-lens module, the sizes of the first upper and lower radial gaps are smaller than the size of the second radial gap.

4. The multi-axis charged particle apparatus according to claim 3, wherein for each magnetic sub-lens module, the first upper and lower radial gaps have equal sizes.

5. The multi-axis charged particle apparatus according to claim 1, further comprising a magnetic stage located below the specimen to sustain the specimen thereon, wherein the magnetic stage magnetically couples with the inner and outer pole-pieces of each magnetic sub-lens to create a strong magnetic field immersion to the specimen.

6. The multi-axis charged particle apparatus according to claim 4, wherein each circular opening in the upper magnetic shielding plate has a shape of upside-down counterbore.

7. The multi-axis charged particle apparatus according to claim 6, wherein a top end of each inner pole-piece extends upward to inside a lower portion of the each upside-down counterbore without touching inner wall thereof, and has an inner diameter equal to or larger than an inner diameter of the upper portion of the upside-down counterbore.

8. The multi-axis charged particle apparatus according to claim 4, wherein bottom ends of each pair of the inner and outer pole-pieces extend downward to inside each circular opening in the lower magnetic shielding plate with the lower radial gap and stop at or above a bottom surface of the lower magnetic shielding plate.

9. The multi-axis charged particle apparatus according to claim 4, wherein for each magnetic sub-lens module includes a first working distance between bottom end of the inner pole-piece and a surface of the specimen, and a second working distance between bottom end of the outer pole-piece and the surface of the specimen.

10. The multi-axis charged particle apparatus according to claim 9, wherein the first working distance is shorter than the second working distance.

11. The multi-axis charged particle apparatus according to claim 4, wherein for the plurality of magnetic sub-lens modules, the second radial gap are identical to each other.

12. The multi-axis charged particle apparatus according to claim 11, wherein for the plurality of magnetic sub-lens modules, the first upper and lower radial gaps of the sub-lens modules located on a central portion of the pair of parallel magnetic conductor plates have sizes smaller than those located on a peripheral portion of the pair of parallel magnetic conductor plates.

13. The multi-axis charged particle apparatus according to claim 12, wherein for the plurality of through round holes, the holes located on the central portion of the pair of parallel magnetic conductor plates have inner diameters smaller than those located on the peripheral portion of the pair of parallel magnetic conductor plates.

14. The multi-axis charged particle apparatus according to claim 12, wherein for the plurality of inner and outer pole-pieces, the pole-pieces located on the central portion of the pair of parallel magnetic conductor plates have outer diameters larger than those located on the peripheral portion of the pair of parallel magnetic conductor plates.

15. The multi-axis charged particle apparatus according to claim 1, wherein for each pair of magnetic rings, the upper magnetic ring has a cylindrical shape or funnel shape whose narrow bottom end is inside the corresponding lower magnetic ring.

16. The multi-axis charged particle apparatus according to claim 1, wherein the pair of parallel magnetic conductor plates, the plurality of magnetic rings, the upper magnetic shielding plate, the lower magnetic shielding plate, the first magnetic shielding tube, the second magnetic shielding tube, the third magnetic shielding tube, the fourth magnetic shielding tube, and the magnetic shielding house are set at ground potential.

17. The multi-axis charged particle apparatus according to claim 16, wherein each charged particle source is an electron source at a negative potential.

18. The multi-axis charged particle apparatus according to claim 17, wherein the specimen and the magnetic stage are set at a negative potential higher than the potential of each electron source.

19. The multi-axis charged particle apparatus according to claim 18, wherein each flat electrode is set at a potential equal to or higher than the potential of the specimen.

20. The multi-axis charged particle apparatus according to claim 19, wherein the plurality of flat electrodes is set at same potential.

21. The multi-axis charged particle apparatus according to claim 20, wherein the plurality of flat electrodes is united to be a single large flat electrode which includes all of the circle orifices of the plurality of flat electrodes.

22. The multi-axis charged particle apparatus according to claim 19, wherein the plurality of flat electrodes is set at different potentials.

23. The multi-axis charged particle apparatus according to claim 1, further comprising a fifth magnetic tube between the detector and the beam limit aperture.

* * * * *